United States Patent
Olson et al.

(10) Patent No.: US 11,377,626 B2
(45) Date of Patent: Jul. 5, 2022

(54) SOLID ENZYMATIC DETERGENT COMPOSITIONS AND METHODS OF USE AND MANUFACTURE

(71) Applicant: Ecolab USA Inc., Saint Paul, MN (US)

(72) Inventors: Erik C. Olson, Saint Paul, MN (US); David Riehm, Saint Paul, MN (US); Carter M. Silvernail, Saint Paul, MN (US); Olivia N. L. Finster, Saint Paul, MN (US); Michael S. Rischmiller, Saint Paul, MN (US); Timothy Meier, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 197 days.

(21) Appl. No.: 16/297,049

(22) Filed: Mar. 8, 2019

(65) Prior Publication Data
US 2019/0276773 A1    Sep. 12, 2019

Related U.S. Application Data

(60) Provisional application No. 62/807,070, filed on Feb. 18, 2019, provisional application No. 62/640,324, filed on Mar. 8, 2018.

(51) Int. Cl.
*C11D 3/386* (2006.01)
*C11D 3/10* (2006.01)
(Continued)

(52) U.S. Cl.
CPC ............ *C11D 3/38609* (2013.01); *A61L 2/23* (2013.01); *C11D 1/66* (2013.01); *C11D 1/722* (2013.01);
(Continued)

(58) Field of Classification Search
CPC .................................. C11D 3/10; C11D 3/30
See application file for complete search history.

(56) References Cited

U.S. PATENT DOCUMENTS

| 5,151,208 A | 9/1992 | Huijben et al. |
| 5,340,501 A * | 8/1994 | Steindorf ................. C11D 3/33 510/224 |

(Continued)

FOREIGN PATENT DOCUMENTS

| JP | 6299196 A | 10/1994 |
| JP | 987698 A | 3/1997 |

(Continued)

OTHER PUBLICATIONS

Leaper et al., "A comparison of compacting and caking behaviour of carbonate-based washing powders", Drying Technology, vol. 31(7), 10 pages, May 2013.
(Continued)

*Primary Examiner* — Liam J Heincer
*Assistant Examiner* — M. Reza Asdjodi
(74) *Attorney, Agent, or Firm* — McKee, Voorhees & Sease, PLC

(57) ABSTRACT

The present disclosure relates to a solid, enzymatic detergent compositions and methods of making and using the same. In a preferred embodiment, the detergent compositions are particularly useful for cleaning medical and dental instruments. In a preferred embodiment the compositions are particularly use for cleaning ware.

23 Claims, 7 Drawing Sheets

| Formula | 5 min | 10 min | 15 min | 20 min | 25 min | 30 min | Dried |
|---|---|---|---|---|---|---|---|
| Competitive Formula A, 2000 ppm | | | | | | | |
| Competitive Formula B, 2000 ppm | | | | | | | |
| Exemplary Formula A, 660 ppm | | | | | | | |

(51) Int. Cl.
*C11D 3/30* (2006.01)
*A61L 2/23* (2006.01)
*C11D 3/20* (2006.01)
*C11D 1/722* (2006.01)
*C11D 17/00* (2006.01)
*C11D 3/48* (2006.01)
*C11D 3/33* (2006.01)
*C11D 1/88* (2006.01)
*C11D 1/66* (2006.01)
*C11D 1/94* (2006.01)

(52) U.S. Cl.
CPC ............. *C11D 1/88* (2013.01); *C11D 1/94* (2013.01); *C11D 3/10* (2013.01); *C11D 3/2082* (2013.01); *C11D 3/30* (2013.01); *C11D 3/33* (2013.01); *C11D 3/386* (2013.01); *C11D 3/38627* (2013.01); *C11D 3/38645* (2013.01); *C11D 3/48* (2013.01); *C11D 17/00* (2013.01); *A61L 2202/24* (2013.01)

(56) References Cited

U.S. PATENT DOCUMENTS

| | | | |
|---|---|---|---|
| 5,429,765 A | 7/1995 | Flower | |
| 5,698,508 A | 12/1997 | Nomura et al. | |
| 5,719,111 A * | 2/1998 | van den Brom | C11D 3/3707 510/224 |
| 5,810,944 A | 9/1998 | Smitkowski et al. | |
| 5,861,366 A * | 1/1999 | Ihns | C11D 1/44 510/320 |
| 6,440,922 B1 | 8/2002 | Garnett et al. | |
| 6,440,927 B1 * | 8/2002 | Painter | C11D 3/0052 510/224 |
| 7,153,820 B2 | 12/2006 | Olson et al. | |
| 7,211,552 B1 | 5/2007 | Thoele | |
| 7,442,679 B2 * | 10/2008 | Stolte | C11D 11/0082 510/445 |
| 7,491,362 B1 | 2/2009 | Geret et al. | |
| 7,597,766 B2 | 10/2009 | McRae et al. | |
| 7,759,300 B2 | 7/2010 | Besse et al. | |
| 7,902,137 B2 | 3/2011 | Kneipp et al. | |
| 7,998,406 B2 | 8/2011 | Geret et al. | |
| 8,420,584 B2 | 4/2013 | Thoele et al. | |
| 8,921,295 B2 | 12/2014 | Kneipp et al. | |
| 2003/0040458 A1* | 2/2003 | Olson | C11D 3/06 510/446 |
| 2004/0072714 A1* | 4/2004 | Tarara | C11D 3/38645 510/392 |
| 2005/0233920 A1* | 10/2005 | Stolte | C11D 17/0047 510/147 |
| 2007/0225197 A1 | 9/2007 | Kruse et al. | |
| 2009/0176687 A1* | 7/2009 | Tjelta | C11D 3/3761 510/445 |
| 2010/0298193 A1* | 11/2010 | Tjelta | C11D 17/0052 510/224 |
| 2012/0083437 A1 | 4/2012 | Choczaj et al. | |
| 2012/0329700 A1* | 12/2012 | Silvernail | C08L 43/02 510/451 |
| 2013/0084626 A1 | 4/2013 | Choczaj et al. | |
| 2013/0130964 A1 | 5/2013 | Besse et al. | |
| 2014/0323385 A1* | 10/2014 | Bartelme | C11D 10/04 510/446 |
| 2015/0119312 A1 | 4/2015 | Sanders et al. | |
| 2015/0132833 A1 | 5/2015 | Chan et al. | |
| 2015/0187130 A1 | 7/2015 | Guskov et al. | |
| 2016/0201013 A1* | 7/2016 | Bartelme | C11D 17/06 510/161 |
| 2017/0158988 A1 | 6/2017 | Lo et al. | |
| 2017/0218306 A1 | 8/2017 | Martinez-Crowley et al. | |
| 2017/0333956 A1 | 11/2017 | Ortmann et al. | |
| 2018/0010068 A1 | 1/2018 | Roerdink Lander et al. | |
| 2018/0015509 A1 | 1/2018 | Carter et al. | |
| 2018/0320110 A1 | 11/2018 | Dotzauer et al. | |
| 2018/0334640 A1* | 11/2018 | Bartelme | C11D 3/10 |
| 2020/0216780 A1* | 7/2020 | Bartelme | C11D 3/044 |

FOREIGN PATENT DOCUMENTS

| | | |
|---|---|---|
| JP | 11302686 A | 11/1999 |
| WO | 9924549 A1 | 5/1999 |
| WO | 02061026 A1 | 8/2002 |
| WO | 03016456 A1 | 2/2003 |
| WO | 2017055254 A1 | 4/2017 |

OTHER PUBLICATIONS

Ecolab USA Inc., "Notification of Transmittal of the International Search Report and The Written Opinion of the International Searching Authority, or the Declaration" in connection with PCT/US2019/021307 filed Mar. 8, 2019, 13 pages, dated Jun. 24, 2019.

* cited by examiner

SOLID ENZYMATIC DETERGENT COMPOSITIONS AND METHODS OF USE AND MANUFACTURE

CROSS-REFERENCE TO RELATED APPLICATIONS

This application claims priority to Provisional Application U.S. Ser. No. 62/640,324, filed on Mar. 8, 2018 and Provisional Application U.S. Ser. No. 62/807,070 filed on Feb. 18, 2019, both of which are herein incorporated by reference in their entirety.

TECHNICAL FIELD

The disclosure relates to solid, enzymatic detergent compositions and methods of making and using the same.

BACKGROUND

Incorporation of enzymes into solid detergent compositions has proven difficult. Many enzymes are in liquid form and are not readily incorporated into solid compositions while maintaining efficacy. This has been true in many industries, including, for example, the formulation of laundry, warewash, and medical instrument cleaning compositions.

Medical and dental instruments must be thoroughly cleaned and sanitized before being reused. Cleaning processes include multiple steps, some of which may be automated and some of which may be manual. The instruments cleaned may be heavily soiled with blood, protein and fat based soils, or sharp, small or irregular shaped. The process of washing and disinfecting becomes complicated when blood or other soils dry on the instruments. The body fluids, such as blood, lipids and synovial fluids from joints adhere to the items used during a procedure. As these fluids dry, the adhesion gets stronger and the fluids get harder to dissolve using ordinary cleaning methods. Blood, in particular, becomes much more difficult to remove once it has dried. Enzymes can help break these soils down. Currently, all enzymatic automated or automatic and manual instrument detergents on the market are liquid detergents, which must be sold in sturdy containers and constitute a spill risk.

Accordingly, it is an objective of the claimed invention to develop solid enzymatic detergents.

A further object of the invention is providing a solid enzymatic detergent that remains stable.

A further object of the invention is providing a solid enzymatic detergent that can reduce packaging and safety concerns related to spillage.

Other objects, advantages and features of the detergent compositions and methods will become apparent from the following specification taken in conjunction with the accompanying figures.

BRIEF SUMMARY OF THE PREFERRED EMBODIMENT

An advantage of the enzymatic detergent compositions is that they can be prepared in stable solid form while retaining their cleaning efficacy. A preferred embodiment is a solid detergent composition comprising an alkali metal carbonate, an acid, an enzyme, and a surfactant, wherein the surfactant is a nonionic surfactant, amphoteric surfactant, or mixtures thereof, and wherein upon dilution the composition provides a pH of between 6 and 11.

A more preferred embodiment is a solid detergent composition comprising between about 15 wt. % and about 75 wt. % of an alkali metal carbonate, between about 10 wt. % and about 50 wt. % of a polycarboxylic acid or salt thereof, wherein the polycarboxylic acid or salt thereof has between 2 and 4 carboxyl groups, between about 0.1 wt. % and about 25 wt. % of an enzyme, and between about 0.5 wt. % and about 25 wt. % of a surfactant, wherein the surfactant is a nonionic surfactant, amphoteric surfactant, or mixtures thereof; wherein upon dilution the composition provides a pH of between about 6 and about 10.5; and wherein the composition is a cast solid, extruded solid, molded solid, or pressed solid.

Another preferred embodiment is found in a method of cleaning a surface comprising (a) diluting a solid detergent composition comprising an alkali metal carbonate, an acid, an enzyme, and a surfactant, wherein the surfactant is a nonionic surfactant, amphoteric surfactant, or mixtures thereof to form a cleaning solution having a pH of between about 6 and about 11; (b) contacting a surface with the cleaning solution; wherein the contacting step is performed at a temperature between about 50° F. and about 180° F.; and (c) rinsing with water.

Another preferred embodiment is found in a method of cleaning a medical and/or dental instrument comprising (a) diluting a solid detergent composition comprising an alkali metal carbonate, an acid, an enzyme, and a surfactant, wherein the surfactant is a nonionic surfactant, amphoteric surfactant, or mixtures thereof to form a cleaning solution having a pH of between about 6 and about 9.5; (b) contacting an instrument with the cleaning solution; wherein the contacting step is performed at a temperature between about 50° F. and about 150° F.; and (c) rinsing with water.

Another preferred embodiment is found in a method of cleaning ware comprising (a) diluting a solid detergent composition comprising an alkali metal carbonate, an acid, an enzyme, and a surfactant, wherein the surfactant is a nonionic surfactant, amphoteric surfactant, or mixtures thereof to form a cleaning solution having a pH of between about 8 and about 11; (b) contacting a surface with the cleaning solution; wherein the contacting step is performed at a temperature between about 60° F. and about 180° F.; and (c) rinsing with water.

While multiple embodiments are disclosed, still other embodiments of the present invention will become apparent to those skilled in the art from the following detailed description, which shows and describes illustrative embodiments of the invention.

Accordingly, the figures and detailed description are to be regarded as illustrative in nature and not restrictive.

Figure 1:
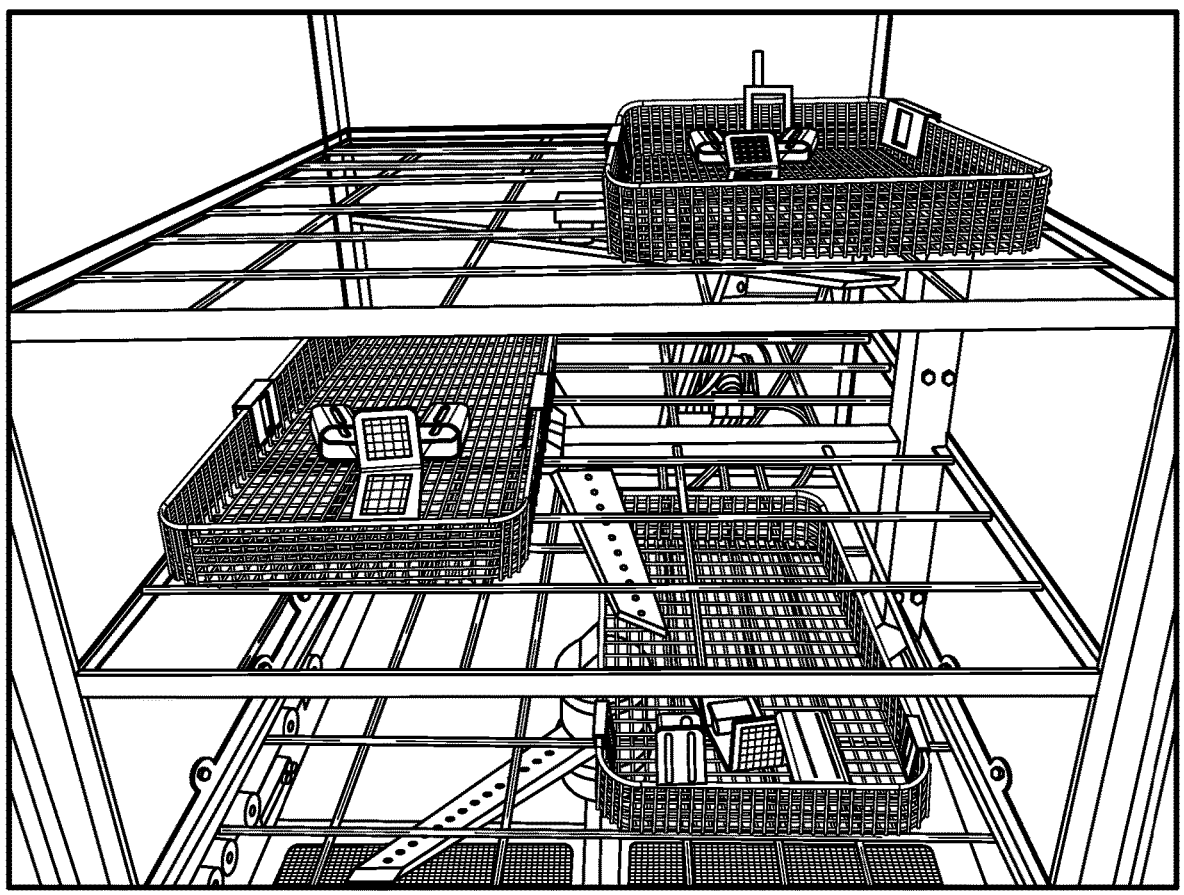
FIG. 1 is a photograph depicting an exemplary arrangement of the wash check trays in the Washer-Disinfector.

Various embodiments of the present invention will be described in detail with reference to the figures. Reference to various embodiments does not limit the scope of the invention. Figures represented herein are not limitations to the various embodiments described herein and are presented for exemplary illustration of a preferred embodiment.

DETAILED DESCRIPTION OF THE PREFERRED EMBODIMENT

The present disclosure relates to solid enzymatic cleaning compositions, their methods of manufacture, and their methods of use. In a preferred embodiment, the solid enzymatic cleaning compositions are useful for cleaning medical and/or dental instruments. In a preferred embodiment, the solid detergent compositions are useful for cleaning ware. The detergent compositions described herein have many advantages over existing detergent compositions, including those for cleaning ware or medical and dental instruments. For example, the compositions described herein are stable in solid form and the components retain their efficacy upon dilution. Moreover, prior enzymatic detergents for cleaning medical and dental instruments have been confined to liquid formulations due to stability and efficacy problems.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The embodiments of this invention are not limited to particular medical and dental instruments and methods of cleaning the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in their SI accepted forms.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

References to elements herein are intended to encompass any or all of their oxidative states and isotopes.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein, the term "instrument" refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, stethoscopes, arthroscopes, and related equipment, and the like, or combinations thereof.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrylonitrile-butadiene-styrene polymers (ABS), and polysulfone polymers (PS). Another exemplary plastic that can be cleaned using the compounds and compositions of the invention include polyethylene terephthalate (PET).

The term "weight percent," "wt. %," "wt-%," "percent by weight," "% by weight," and variations thereof, as used herein, refer to the concentration of a substance as the weight of that substance divided by the total weight of the composition and multiplied by 100.

The methods and compositions described herein may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Solid Enzymatic Detergent Compositions

Described herein are the ingredients and methods of making and using solid enzymatic detergent compositions. Certain preferred embodiments of the solid enzymatic detergent compositions are useful for cleaning medical and dental instruments. Certain preferred embodiments of the solid enzymatic detergent compositions are useful for cleaning ware. The solid enzymatic detergent compositions can be prepared in a variety of solid forms, including, a cast solid, an extruded solid, a molded solid, a powder, or a pressed solid. Preferably, the solid enzymatic detergent is a powder or pressed solid.

Preferably, the solid enzymatic detergent compositions dilute to a near neutral pH to moderately alkaline pH. For example, embodiments of the solid detergent compositions will provide a pH of between about 6 and about 11 upon dilution. In a preferred embodiment, of the solid enzymatic detergents will provide a pH between about 6 and about 11 upon dilution, preferably between about 6 and about 9, more preferably between about 6.5 and about 8.5, most preferably between about 6.8 and about 8. In another embodiment, the solid enzymatic detergents will provide a pH between about 7.5 and about 11, more preferably between about 8 and about 10.5, more preferably between about 8.5 and about 10, most preferably between about 9 and about 9.5.

Preferably, the solid enzymatic detergent compositions are low foaming or non-foaming. As used herein, non-foaming means that the composition forms no foam upon dilution, or that it forms foam which breaks in less than 10 seconds, more preferably less than 5 seconds at a temperature between about 50° F. and about 180° F. As used herein, low foaming means that the composition forms foam which breaks in less than 30 seconds, more preferably less than 20 seconds, most preferably less than 15 seconds at a temperature between about 50° F. and about 150° F.

The solid enzymatic detergent compositions comprise a solidification matrix, enzyme, and surfactant. Preferably the solidification matrix comprises an alkali metal carbonate and an acid. Preferably, the surfactant is a low foaming or non-foaming surfactant. In a preferred embodiment, the solid enzymatic detergent compositions also comprise a preservative and/or a water conditioning agent. Various additional ingredients can be added to the solid enzymatic detergent compositions.

Solidification Matrix

The compositions of the invention comprise a solidification matrix. The solidification matrix can be comprised of an alkali metal carbonate and an acid. When combined together in the composition, the alkali metal carbonate and acid form a solidification matrix. Surprisingly, it has been found that the solidification matrix formed by the alkali metal carbonate and acid can form a stable solid composition containing the enzyme and low foaming surfactants that retains the efficacy of the components in the composition, including, the enzyme and surfactants. This is a significant improvement as it has not been possible to formulate a solid neutral enzymatic cleaner that is stable and where the components retain their efficacy.

Acid

The compositions comprise an acid or salt thereof. The acid is a part of the solidification matrix. Preferably the acid has an aqueous solubility between 0.1 g/L and 1500 g/L at 20° C., more preferably between 0.25 g/L and 500 g/L at 20° C., most preferably between 0.25 and 100 g/L at 20° C. As used herein, the g/L description refers to the mass of acid added with sufficient aqueous medium (e.g., water) to form one liter of solution. Preferably the acid is a polycarboxylic acid. More preferably, the acid is a polycarboxylic acid having between 2 and 4 carboxyl groups. More preferably the polycarboxylic acid is a dicarboxylic acid or a tricarboxylic acid. Preferred acids include, but are not limited to, adipic acid, citric acid, ethylenediamine tetra acetic acid, isocitric acid, glutamic acid, glutaric acid, malic acid, propane-1,2,3-tricarboxylic acid, succinic acid, tartartic acid, salts of the foregoing, and mixtures thereof.

Preferably the acid is in an amount between about 10 wt. % and about 50 wt. %, between about 12 and about 50 wt. %, more preferably between about 15 wt. % and about 50 wt. %, more preferably between about 15 wt. % and about 45 wt. %, most preferably between about 20 wt. % and about 45 wt. %.

Alkali Metal Carbonate

The compositions comprise an alkali metal carbonate. The alkali metal carbonate is part of the solidification matrix. Preferred alkali metal carbonates include, but are not limited to, sodium carbonate, potassium carbonate, bicarbonate, sesquicarbonate, and mixtures thereof.

Preferably the alkali metal carbonate is in an amount between about 15 wt. % and about 75 wt. %, more preferably between about 20 wt. % and about 70 wt. %, most preferably between about 25 wt. % and about 70 wt. %.

Enzyme

The solid detergent compositions comprise one or more enzymes. Preferred enzymes include, amylases, cellulases, lipases, proteases, and combinations of the same. Most preferably, the enzyme comprises a protease. The enzyme is preferably in an amount between about 0.1 wt. % and about 25 wt. %, more preferably between about 0.5 wt. % and about 20 wt. %, most preferably between about 1 wt. % and about 15 wt. %.

Amylases

Any amylase or mixture of amylases, from any source, can be used in the solid detergent compositions, provided that the selected enzyme is stable in the desired pH range (between about 6 and about 9). For example, the amylase enzymes can be derived from a plant, an animal, or a microorganism such as a yeast, a mold, or a bacterium. Preferred amylase enzymes include, but are not limited to, those derived from a *Bacillus*, such as *B. licheniformis, B. amyloliquefaciens, B. subtilis,* or *B. stearothermophilus*. Amylase enzymes derived from *B. subtilis* are most preferred. The amylase can be purified or a component of a microbial extract, and either wild type or variant (either chemical or recombinant). Preferred amylases are commercially available under the trade name Stainzyme® available from Novozymes.

Cellulases

Any cellulase or mixture of cellulases, from any source, can be used in the solid detergent compositions, provided that the selected enzyme is stable in the desired pH range (between about 6 and about 9). For example, the cellulase enzymes can be derived from a plant, an animal, or a microorganism such as a fungus or a bacterium. Preferred cellulase enzymes include, but are not limited to, those derived from *Humicola insolens, Humicola* strain DSM1800, or a cellulase 212-producing fungus belonging to the genus *Aeromonas* and those extracted from the hepatopancreas of a marine mollusk, *Dolabella auricula solander*. The cellulase can be purified or a component of a microbial extract, and either wild type or variant (either chemical or recombinant).

Lipases

Any lipase or mixture of lipases, from any source, can be used in the solid detergent compositions, provided that the selected enzyme is stable in the desired pH range (between about 6 and about 9). For example, the lipase enzymes can be derived from a plant, an animal, or a microorganism such as a fungus or a bacterium. Preferred protease enzymes include, but are not limited to, the enzymes derived from a *Pseudomonas*, such as *Pseudomonas stutzeri* ATCC 19.154, or from a *Humicola*, such as *Humicola lanuginosa* (typically produced recombinantly in *Aspergillus oryzae*). The lipase can be purified or a component of a microbial extract, and either wild type or variant (either chemical or recombinant).

Proteases

Any protease or mixture of proteases, from any source, can be used in the solid detergent compositions, provided that the selected enzyme is stable in the desired pH range (between about 6 and about 9). For example, the protease enzymes can be derived from a plant, an animal, or a microorganism such as a yeast, a mold, or a bacterium. Preferred protease enzymes include, but are not limited to, the enzymes derived from *Bacillus subtilis, Bacillus licheniformis* and *Streptomyces griseus*. Protease enzymes derived from *B. subtilis* are most preferred. The protease can be purified or a component of a microbial extract, and either wild type or variant (either chemical or recombinant). Exemplary proteases are commercially available under the following trade names Alcalase®, Blaze®, Savinase®, Esperase®, and Progress UNO™ (also sold under the name Evens DUO') each available from Novozymes.

Other Enzymes

The solid detergent compositions can comprise additional enzymes in addition to the foregoing. Additional suitable enzymes can include, but are not limited to, cutinases, peroxidases, gluconases, or mixtures thereof.

Surfactant

The solid enzymatic compositions can comprise one or more surfactants. Preferably, the surfactants are low foaming or non-foaming. Preferred surfactants include, but are not limited to, amphoteric surfactants, nonionic surfactants, and mixtures thereof. Preferably, the surfactant is in an amount between about 0.1 wt. % and about 25 wt. %, more preferably in an amount between about 0.5 wt. % and about 20 wt. %, most preferably between about 1 wt. % and about 15 wt. %.

Amphoteric Surfactants

The solid enzymatic compositions can comprise an amphoteric surfactant. Amphoteric surfactants contain both a basic and an acidic hydrophilic group and an organic hydrophobic group. These ionic entities may be any of the anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants are subdivided into two major classes. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes. Preferred amphoteric surfactants for use in the solid enzymatic compositions can be broadly described as derivatives of aliphatic secondary, tertiary, or quaternary amines, in which the aliphatic radical may be straight chain or branched and wherein one of the aliphatic substituents contains from 6 to 18 carbon atoms and one contains an anionic water solubilizing group, e.g., carboxy, sulfo, sulfato, phosphato, or phosphono. Preferred amphoteric surfactants include amine oxides.

Amine oxides are tertiary amine oxides corresponding to the general formula:

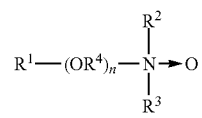

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 18 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Suitable amine oxides can include those selected from the coconut or tallow alkyl di-(lower alkyl) amine oxides, specific examples of which are decyldimethylamine oxide, octyldimethylamine oxide, dodecyldimethylamine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

More preferred are amphoteric surfactants wherein one substituent of the central amine is an aliphatic radical which contains 6 to 11 carbons, or most preferably 8 to 10 carbons, which is either directly attached to the amine or, more preferably, attached to an amidopropyl or alkoxypropyl group which in turn is attached to the amine. Additionally, in the more preferred amphoteric surfactants, one or more substituents of the central amine contain an anionic carboxy group.

Long chain imidazole derivatives having application in the present invention generally have the general formula:

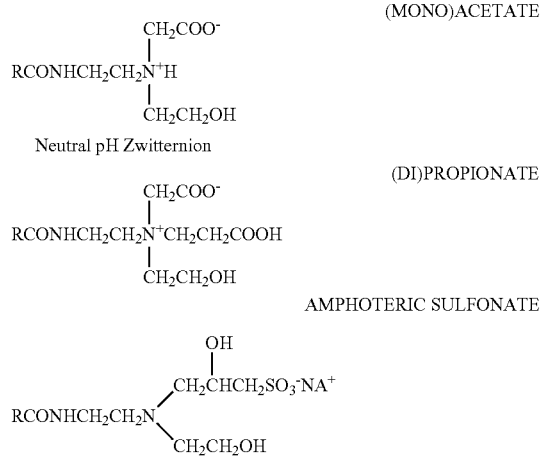

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Coco-amphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na$)$_2$—$CH_2$—$CH_2$—OH or $C_{12}$-alkyl-C(O)—N(H)—$CH_2$—$CH_2$—$N^+$($CH_2$—$CO_2Na$)$_2$—$CH_2$—$CH_2$—OH.

Preferred surfactants include caprylamidopropyl betaine and disodium alkyl hydroxypropyl iminodipropionate. A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated by reference in their entirety.

Nonionic Surfactants

Nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Suitable nonionic surfactants include the following:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Such compounds can include, by way of example, an EO/PO capped alkoxylated glycerol, wherein the EO groups are between 25 wt. % and 50 wt. % of the surfactant, more preferably between about 30 wt. % and about 50 wt. % of the surfactant. Pluronic® compounds are difunctional (two reactive hydrogens). Tetronic® compounds are tetra-functional block copolymers.

2. Condensation products of one mole of alkyl phenol wherein the alkyl chain, of straight chain or branched chain configuration, or of single or dual alkyl constituent, contains from 8 to 18 carbon atoms with from 3 to 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from 6 to 24 carbon atoms with from 3 to 50 moles of ethylene oxide. The alcohol moiety can consist of mixtures of alcohols in the above delineated carbon range or it can consist of an alcohol having a specific number of carbon atoms within this range. Examples of like commercial surfactants are available under the trade names Neodol® manufactured by Shell Chemical Co. and Alfonic® manufactured by Vista Chemical Co.

4. Condensation products of one mole of saturated or unsaturated, straight or branched chain carboxylic acid having from 8 to 18 carbon atoms with from 6 to 50 moles of ethylene oxide. The acid moiety can consist of mixtures of acids in the above defined carbon atom range or it can consist of an acid having a specific number of carbon atoms within the range. Examples of commercial compounds of this chemistry are available on the market under the trade names Nopalcol® manufactured by Henkel Corporation and Lipopeg® manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols can be used. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions containing amylase and/or lipase enzymes because of potential incompatibility.

Examples of nonionic low foaming surfactants include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. These reverse Pluronics® are manufactured by BASF Corporation under the trade name Pluronic® R surfactants. Likewise, the Tetronic® R surfactants are produced by BASF Corporation by the sequential addition of ethylene oxide and propylene oxide to ethylenediamine.

6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

7. The alkylphenoxypolyethoxyalkanols of U.S. Pat. No. 2,903,486 issued Sep. 8, 1959 to Brown et al. and represented by the formula

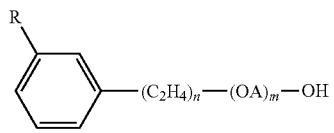

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from 1 to 6 carbon atoms and one reactive hydrogen atom, n has an average value of at least 6.4, as determined by hydroxyl number and m has a value such that the oxyethylene portion constitutes 10% to 90% by weight of the molecule.

The conjugated polyoxyalkylene compounds described in U.S. Pat. No. 2,674,619, issued Apr. 6, 1954 to Lundsted et al. having the formula $Y[(C_3H_6O_n(C_2H_4O)_mH]_x$ wherein Y is the residue of an organic compound having from 2 to 6 carbon atoms and containing x reactive hydrogen atoms in which x has a value of at least 2, n has a value such that the molecular weight of the polyoxypropylene hydrophobic base is at least 900 and m has value such that the oxyethylene content of the molecule is from 10% to 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional useful conjugated polyoxyalkylene surface-active agents correspond to the formula: $P[(C_3H_6O)_n(C_2H_4O)_mH]_x$ wherein P is the residue of an organic compound having from 8 to 18 carbon atoms and containing x reactive hydrogen atoms in which x has a value of 1 or 2, n has a value such that the molecular weight of the polyoxyethylene portion is at least 44 and m has a value such that the oxypropylene content of the molecule is from 10% to 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants include those having the structural formula $R_2CONR_1Z$ in which: $R_1$ is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction, such as a glycityl moiety.

9. The alkyl ethoxylate condensation products of aliphatic alcohols with from 0 to 25 moles of ethylene oxide are suitable. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-$C_{18}$ mixed ethoxylated and propoxylated fatty alcohols are suitable surfactants, particularly those that are water soluble. Suitable ethoxylated fatty alcohols include the $C_{10}$-$C_{18}$ ethoxylated fatty alcohols with a degree of ethoxylation of from 3 to 50.

11. Further exemplary nonionic surfactants suitable for the compositions can include alkyl polyglucosides. Alkyl polyglucosides are a type of alkyl polyglycoside derived from a glucose-based polymer. An alkyl polyglucoside, as used herein in this disclosure, is a molecule having one to ten glucose units backbone and at least one alkyl group attached one of the OH groups and has a generic structure of

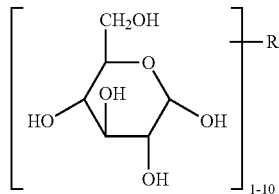

wherein R is an alkyl group and can be attached to any or all of the OH group in the molecule. A cationic alkyl polyglucoside, as used herein in this disclosure, is an alkyl polyglucoside having at least one cationic group in its alkyl group(s).

Preferably, the alkyl group has a carbon chain length between about 1 and about 20 carbons, more preferably between about 2 and about 18 carbons, and most preferably between about 4 and about 16 carbons.

12. Fatty acid amide surfactants include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or —$(C_2H_4O)_xH$, where x is in the range of from 1 to 3.

13. Nonionic surfactants also include the class defined as alkoxylated amines or, most particularly, alcohol alkoxylated/aminated/alkoxylated surfactants. These nonionic surfactants may be at least in part represented by the general formulae:

$$R^{20}—(PO)_sN-(EO)_tH,$$

$$R^{20}—(PO)_sN-(EO)_tH(EO)_tH, \text{ and}$$

$$R^{20}—N(EO)_tH;$$

in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, and t is 1-10, preferably 2-5. Other variations on the scope of these compounds may be represented by the alternative formula:

$$R^{20}—(PO)_v—N[(EO)_wH][(EO)_zH]$$

in which $R^{20}$ is as defined above, v is 1 to 20 (e.g., 1, 2, 3, or 4 (preferably 2)), and w and z are independently 1-10, preferably 2-5.

14. Reverse polyoxyalkylene block copolymer(s) (also known as alkoxylated block copolymer(s)). The reverse polyoxyalkylene block copolymers, especially -(EO)$_e$—(PO)$_p$ block copolymers, are effective in preventing or minimizing any normal foaming activity of other components. Because of their better water-solubility characteristics, the reverse polyoxyethylene-polyoxypropylene (i.e., reverse -(EO)$_e$—(PO)$_p$) block copolymers are preferred over other reverse polyoxyalkylene block copolymers, such as those that contain polyoxybutylene blocks.

The polyoxyalkylene block copolymers useful in the present compositions can be formed by reacting alkylene oxides with initiators. Preferably, the initiator is multifunctional because of its use results in "multibranch" or "multiarm" block copolymers. For example, propylene glycol (bifunctional), triethanol amine (trifunctional), and ethylenediamine (tetrafunctional) can be used as initiators to initiate polymerization of ethylene oxide and propylene oxide to produce reverse block copolymers with two branches (i.e., arms or linear units of polyoxyalkylenes), three branches, and four branches, respectively. Such initiators may contain carbon, nitrogen, or other atoms to which arms or branches, such as blocks of polyoxyethylene (EO)$_e$, polyoxypropylene (PO)$_p$, polyoxybutylene (BO)$_b$, -(EO)$_e$—(PO)$_p$, -(EO)$_e$—(BO)$_b$, or -(EO)$_3$—(PO)$_p$—(BO)$_b$, can be attached. Preferably, the reverse block copolymer has arms or chains of polyoxyalkylenes that are attached to the residues of the initiators contain end blocks of -(EO)$_x$—(PO)$_y$, which have ends of polyoxypropylene (i.e., —(PO)$_y$), wherein x is about 1 to 1000 and y is about 1 to 500, more preferably x is about 5 to 20 and y is about 5 to 20.

The reverse block copolymer can be a straight chain, such as a three-block copolymer, $$(PO)_y\text{-}(EO)_x\text{—}(PO)_y$$

wherein x is about 1 to 1000, preferably about 4 to 230; and y is about 1 to 500, preferably about 8 to 27. Such a copolymer can be prepared by using propylene glycol as an initiator and adding ethylene oxide and propylene oxide. The polyoxyalkylene blocks are added to both ends of the initiator to result in the block copolymer. In such a linear block copolymer, generally the central (EO)$_x$ contains the residue of the initiator and x represents the total number of EO on both sides of the initiator. Generally, the residue of the initiator is not shown in a formula such as the three-block copolymer above because it is insignificant in size and in contribution to the property of the molecule compared to the polyoxyalkylene blocks. Likewise, although the end block of the polyoxyalkylene block copolymer terminates in a —OH group, the end block is represented by —(PO)$_p$, -(EO)$_x$, —(PO)$_y$, and the like, without specifically showing the —OH at the end. Also, x, y, and z are statistical values representing the average number of monomer units in the blocks.

The reverse polyoxyalkylene block copolymer can have more than three blocks, an example of which is a five-block copolymer,

(PO)$_z$-(EO)$_y$—(PO)$_x$-(EO)$_y$—(PO)$_z$ wherein x is about 1 to 1,000, preferably about 7 to 21; y is about 1 to 500, preferably about 10 to 20; and z is about 1 to 500, preferably about 5 to 20.

A chain of blocks may have an odd or even number of blocks. Also, in other embodiments, copolymers with more blocks, such as, six, seven, eight, and nine blocks, etc., may be used as long as the end polyoxyalkylene block is either (PO)$_p$ or (BO)$_b$. As previously stated, the reverse -(EO)$_e$—(PO)$_p$ block copolymer can also have a branched structure having a trifunctional moiety T, which can be the residue of an initiator. The block copolymer is represented by the formula:

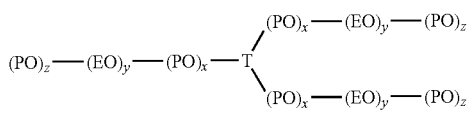

wherein x is about 0 to 500, preferably about 0 to 10; y is about 1 to 500, preferably about 5 to 12, and z is about 1 to 500, preferably about 5 to 10.

Preferred nonionic surfactants include, but are not limited to, reverse Pluronic surfactant having (PO)(EO)(PO) structure and an average molecular weight of less than 3000 g/mole, more preferably less than 2800 g/mole, still more preferably less than 2500 g/mole, wherein the cloud point of a 1% aqueous solution of the surfactant is greater than 30° C., more preferably greater than 35° C., still more preferably greater than 40° C., and most preferably greater than 45° C.

15. Branched Alcohol Alkoxylates

Branched alcohol athoxylate nonionic surfactants are also suitable for the compositions disclosed herein. Preferred branched alcohol alkoxylates include, but are not limited to, Guerbet alcohol alkoxylates having alkoxylation of:

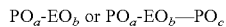

PO$_a$-EO$_b$ or PO$_a$-EO$_b$—PO$_c$ wherein a is between about 1 and about 10; wherein b is between about 1 and about 14; and wherein c is between about 1 and about 20; and wherein the branched alkyl group has between about 6 and about 20 carbons, more preferably between about 6 and about 18, most preferably between about 8 and about 16.

Additional Ingredients

The solid enzymatic compositions can comprise a number of additional ingredients. The additional ingredients can be added in an amount sufficient to impart the desired property or functionality. Exemplary additional ingredients, include, but are not limited to, alkalinity sources, aminocarboxylates, corrosion inhibitors, defoamers, dyes, enzyme stabilizers, fragrances, phosphonates, preservatives, water conditioning agents, and combinations thereof.

Alkalinity Source

The compositions can optionally comprise an alkalinity source in addition to the carbonate included in the solidification matrix. Preferred alkalinity sources, include, but are not limited to, alkali metal hydroxides, metal silicates, metal borates, and organic alkalinity sources. If the compositions comprise an optional alkalinity source, it is preferably in an amount between about 0.01 wt. % and about 25 wt. %, more preferably between about 0.1 wt. % and about 20 wt. %, most preferably between about 0.5 wt. % and about 10 wt. %.

Exemplary alkali metal hydroxides that can be used include, but are not limited to sodium, lithium, or potassium hydroxide. Exemplary metal silicates that can be used include, but are not limited to, sodium or potassium silicate or metasilicate. Exemplary metal borates include, but are not limited to, sodium or potassium borate. Organic alkalinity sources are often strong nitrogen bases including, for example, ammonia (ammonium hydroxide), amines, alkanolamines, and amino alcohols. Typical examples of amines include primary, secondary or tertiary amines and diamines carrying at least one nitrogen linked hydrocarbon group, which represents a saturated or unsaturated linear or branched alkyl group having at least 10 carbon atoms and preferably 16-24 carbon atoms, or an aryl, aralkyl, or alkaryl group containing up to 24 carbon atoms, and wherein the optional other nitrogen linked groups are formed by optionally substituted alkyl groups, aryl group or aralkyl groups or polyalkoxy groups. Typical examples of alkanolamines include monoethanolamine, monopropanolamine, diethanolamine, dipropanolamine, triethanolamine, tripropanolamine and the like. Typical examples of amino alcohols include 2-amino-2-methyl-1-propanol, 2-amino-1-butanol, 2-amino-2-methyl-1,3-propanediol, 2-amino-2-ethyl-1,3-propanediol, hydroxymethyl aminomethane, and the like.

Aminocarboxylates

In an aspect, the detergent compositions include an aminocarboxylate (or aminocarboxylic acid materials). In a preferred aspect, the aminocarboxylates include aminocarboxylic acid materials containing little or no NTA. Exemplary aminocarboxylates include, for example, N-hydroxyethylaminodiacetic acid, ethylenediaminetetraacetic acid (EDTA), methylglycinediacetic acid (MGDA), hydroxyethylenediaminetetraacetic acid, diethylenetriaminepentaacetic acid, N-hydroxyethyl-ethylenediaminetriacetic acid (HEDTA), glutamic acid N,N-diacetic acid (GLDA), diethylenetriaminepentaacetic acid (DTPA), Iminodisuccinic acid (IDS), ethylenediamine disuccinic acid (EDDS), 3-hydroxy-2,2-iminodisuccinic acid (HIDS), hydroxyethyliminodiacetic acid (HEIDA) and other similar acids having an amino group with a carboxylic acid substituent. In an aspect, the aminocarboxylate is ethylenediaminetetraacetic acid (EDTA).

If an aminocarboxylate is included in the compositions, it is preferably in an amount between about 0.1 wt. % and about 30 wt. %; more preferably between about 0.5 wt. % and about 25 wt. %, most preferably between about 1 wt. % and 20 wt. %.

Corrosion Inhibitors

The solid detergent compositions can optionally include a corrosion inhibitor. Exemplary corrosion inhibitors include an alkaline metal silicate or hydrate thereof, phosphino succinate, or combination thereof. Exemplary alkali metal silicates include powdered, particulate or granular silicates which are either anhydrous or preferably which contain water of hydration (between about 5 and about 25 wt. %, preferably between about 15 and about 20 wt. % water of hydration). These silicates include sodium silicates and have a Na$_2$O:SiO$_2$ ratio of about 1:1 to about 1:5, respectively. If a corrosion inhibitor is included in the compositions, it is preferably in an amount between about 0.01 wt. % and about 10 wt. %.

Defoamers

The solid detergent compositions can optionally include a defoamer and/or foam inhibitor. The compositions preferably do not foam or have foam that breaks promptly upon formation. Adding a defoamer and/or foam inhibitor can assist in preventing foam and reducing any foam's stability such that it can break promptly.

Suitable defoamers include silicon compounds such as silica dispersed in polydimethylsiloxane, fatty amides, amides, hydrocarbon waxes, fatty acids and soaps thereof, fatty esters, fatty alcohols, fatty acid soaps, sulfates and sulfonates, ethoxylates, vegetable oils, mineral oils and their sulfonated or sulfated derivatives, polyethylene glycol esters, block copolymers, including for example, difunctional block copolymers and polyoxyethylene-polyoxypropylene block copolymers, alkyl phosphates and phosphate esters such as alkyl and alkaline diphosphates, tributyl phosphates, and monostearyl phosphate, halogenated compounds such as fluorochlorohydrocarbons, and the like. If a defoamer is included in the solid detergent compositions, it is preferably present in an amount sufficient to provide the desired defoaming properties. If a defoamer is included in the compositions, it is preferably in an amount between about 0.01 wt. % and about 10 wt. %, more preferably between about 0.1 wt. % and about 8 wt. %, most preferably between about 0.5 wt. % and about 5 wt. %.

Dyes

The solid detergent compositions can optionally include a dye. Preferred dyes, include, but are not limited to, Violet Dye 148 (Keycolour), Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), and Acid Green 25 (Ciba-Geigy).

If a dye is included in the compositions, it is preferably in an amount between about 0.005 wt. % and about 10 wt. %.

Enzyme Stabilizers

The solid detergent compositions can optionally include an enzyme stabilizer. Preferred enzyme stabilizers include boron compounds or a calcium salts. More preferred, the enzyme stabilizers are a boron compound selected from the group consisting of boronic acid, boric acid, borate, polyborate and combinations thereof.

If an enzyme stabilizer is included in the compositions, it is preferably in an amount between about 0.01 wt. % and about 10 wt. %.

Fragrances

The solid detergent compositions can optionally include a fragrance, odorant, or perfume. Preferred fragrances include, but are not limited to, terpenoids such as citronellol, aldehydes such as amyl cinnamaldehyde, a jasmine such as C1S-jasmine or jasmal, vanillin, and the like.

If a fragrance is included in the compositions, it is preferably in an amount between about 0.01 wt. % and about 10 wt. %.

Preservatives

The solid detergent compositions can optionally include a preservative. Suitable preservatives include, but are not limited to, the antimicrobial classes such as phenolics, quaternary ammonium compounds, metal derivatives, amines, alkanol amines, nitro derivatives, analides, organosulfur and sulfur-nitrogen compounds and miscellaneous compounds. Exemplary phenolic agents include pentachlorophenol, orthophenylphenol. Exemplary quaternary antimicrobial agents include benzalconium chloride, cetylpyridiniumchloride, amine and nitro containing antimicrobial compositions such as hexahydro-1,3,5-tris(2-hydroxyethyl)-s-triazine, dithiocarbamates such as sodium dimethyldithiocarbamate, and a variety of other materials known in the art for their microbial properties. Other exemplary preservatives include gluteraldehyde, Bronopol, silver, and isothiazolones such as methylisothiazolinone. Preferred preservatives include those sold under the tradename Neolone™.

If a preservative is included in the compositions, it is preferably in an amount between about 0.01 wt. % and about 10 wt. %.

Phosphonates

In some embodiments, the compositions of the present invention include a phosphonate. Examples of phosphonates include, but are not limited to: phosphinosuccinic acid oligomer (PSO) described in U.S. Pat. Nos. 8,871,699 and 9,255,242; 2-phosphinobutane-1,2,4-tricarboxylic acid (PBTC), 1-hydroxyethane-1,1-diphosphonic acid, $CH_2C(OH)[PO(OH)_2]_2$; aminotri(methylenephosphonic acid), $N[CH_2PO(OH)_2]_3$; aminotri(methylenephosphonate), sodium salt (ATMP), $N[CH_2PO(ONa)_2]_3$; 2-hydroxyethyl-iminobis(methylenephosphonic acid), $HOCH_2CH_2N[CH_2PO(OH)_2]_2$; diethylenetriaminepenta(methylenephosphonic acid), $(HO)_2POCH_2N[CH_2CH_2N[CH_2PO(OH)_2]_2]_2$; diethylenetriaminepenta(methylenephosphonate), sodium salt (DTPMP), $C_9H_{(28-x)}N_3Na_xO_{15}P_5$ (x=7); hexamethylenediamine(tetramethylenephosphonate), potassium salt, $C_{10}H_{(28-x)}N_2K_xO_{12}P_4$ (x=6); bis(hexamethylene)triamine (pentamethylenephosphonic acid). $(HO_2)POCH_2N[(CH_2)_2N[CH_2PO(OH)_2]_2]_2$; monoethanolamine phosphonate (MEAP), diglycolamine phosphonate (DGAP) and phosphorus acid, $H_3PO_3$. Preferred phosphonates are PBTC, HEDP, ATMP and DTPMP. A neutralized or alkali phosphonate, or a combination of the phosphonate with an alkali source prior to being added into the mixture such that there is little or no heat or gas generated by a neutralization reaction when the phosphonate is added is preferred. In one embodiment, however, the composition is phosphorous-free.

If a phosphonate is included in the compositions, it is preferably in an amount between about 0.01 wt. % and about 30 wt. %; more preferably between about 0.5 wt. % and about 25 wt. %, most preferably between about 1 wt. % and 10 wt. %.

Water Conditioning Agents

In an aspect the compositions include at least one water conditioning polymer. In a preferred aspect, the composition comprises a polycarboxylic acid polymer or salt thereof, a phosphate, and optionally additional polymers. In a preferred embodiment, the compositions are phosphate-free. Suitable polycarboxylic acid polymers include those with a molecular weight less from about 400-50,000 g/mol. Suitable polycarboxylic acid polymers include those with a molecular weight between about 400-50,000 g/mol more preferable between about 400-25,000 g/mol and most preferably between about 400-15,000 g/mol.

Polycarboxylic acid polymers can also be referred to as non-phosphorus containing builders. Polycarboxylic acid polymers may include, but are not limited to those having pendant carboxylate (—$CO_2$—) groups such as acrylic acid homopolymers, maleic acid homopolymers, maleic/olefin copolymers, maleic acid terpolymers, sulfonated copolymers or terpolymers, acrylic/maleic copolymers or terpolymers, methacrylic acid homopolymers, methacrylic acid copolymers or terpolymers, acrylic acid-methacrylic acid copolymers, hydrolyzed polyacrylamides, hydrolyzed polymethacrylamides, hydrolyzed polyamide-methacrylamide copolymers, hydrolyzed polyacrylonitriles, hydrolyzed polymethacrylonitriles, hydrolyzed acrylonitrile-methacrylonitrile copolymers and combinations thereof. Preferred polycarboxylic acids or salts thereof include polyacrylic acid homopolymers, polyacrylic acid copolymers, and maleic acid copolymers and maleic acid terpolymers.

In embodiments of the compositions which are not phosphate-free, added water conditioning agents may include, for example a condensed phosphate, a phosphonate, and the like. Some examples of condensed phosphates include sodium and potassium orthophosphate, sodium and potassium pyrophosphate, sodium tripolyphosphate, sodium hexametaphosphate, and the like. A condensed phosphate may also assist, to a limited extent, in solidification of the composition by fixing the free water present in the composition as water of hydration.

In embodiments of the compositions which are not phosphate-free, the compositions may include a phosphonate such as 1-hydroxyethane-1,1-diphosphonic acid $CH_3C(OH)[PO(OH)_2]_2$; aminotri(methylenephosphonic acid) $N[CH_2PO(OH)_2]_3$; aminotri(methylenephosphonate), sodium salt

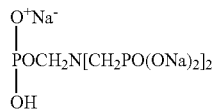

2-hydroxyethyliminobis(methylenephosphonic acid) $HOCH_2 CH_2 N[CH_2 PO(OH)_2]_2$; diethylenetriaminepenta (methylenephosphonic acid) $(HO)_2 POCH_2 N[CH_2 N[CH_2 PO(OH)_2]_2]_2$; diethylenetriaminepenta(methylenephosphonate), sodium salt $C_9 H_{(28-x)} N_3 Na_xO_{15}P_5$ (x=7); hexamethylenediamine(tetramethylenephosphonate), potassium salt $C_{10} H_{(28-x)}N_2K_xO_{12}P_4$ (x=6); bis(hexamethylene)triamine (pentamethylenephosphonic acid) $(HO_2)POCH_2N[(CH_2)_6N[CH_2 PO(OH)_2]_2]_2$; and phosphorus acid $H_3PO_3$. In some embodiments, a phosphonate combination such as ATMP and DTPMP may be used. If a water conditioning agent is included in the compositions, it is preferably in an amount between about 0.1 wt. % and about 30 wt. %; more preferably between about 0.5 wt. % and about 25 wt. %, most preferably between about 1 wt. % and 20 wt. %.

Exemplary Compositions

The compositions as described herein can be prepared as 2-in-1 manual and automatic compositions or as separate manual or automatic formulations. Preferred solid compositions for instrument (medical and dental) are described below in Tables 1B-1D. Table 1E provides an exemplary preferred non-instrument cleaning formulation, e.g., solid warewash formulation. It should be understood these are exemplary formulations and not intended to be limiting.

TABLE 1A

Exemplary Solid Detergent Formulations

| | Preferred Formulation (wt. %) | More Preferred Formulation (wt. %) | Most Preferred Formulation (wt. %) |
|---|---|---|---|
| Alkali metal carbonate | 15-75 | 20-70 | 25-70 |
| Acid | 10-50 | 12-50 | 15-45 |
| Enzyme | 0.1-25 | 0.5-20 | 1-15 |

TABLE 1A-continued

Exemplary Solid Detergent Formulations

| | Preferred Formulation (wt. %) | More Preferred Formulation (wt. %) | Most Preferred Formulation (wt. %) |
|---|---|---|---|
| Surfactant | 0.1-25 | 0.5-20 | 1-15 |
| Optional ingredients | 0-25 | 0.01-20 | 0.1-20 |

TABLE 1B

Exemplary 2-in-1 Instrument Cleaning Formulations

| | Preferred Formulation (wt. %) | More Preferred Formulation (wt. %) | Most Preferred Formulation (wt. %) |
|---|---|---|---|
| Alkali metal carbonate | 15-50 | 20-45 | 25-40 |
| Acid | 10-50 | 15-50 | 20-45 |
| Enzyme | 0.1-25 | 0.5-20 | 1-15 |
| Surfactant | 0.5-25 | 0.5-20 | 1-15 |
| Optional ingredients | 0-25 | 0.01-20 | 0.1-20 |

TABLE 1C

Exemplary Manual Instrument Cleaning Formulations

| | Preferred Formulation (wt. %) | More Preferred Formulation (wt. %) | Most Preferred Formulation (wt. %) |
|---|---|---|---|
| Alkali metal carbonate | 20-60 | 20-50 | 25-45 |
| Acid | 10-50 | 15-50 | 20-45 |
| Enzyme | 0.1-25 | 0.5-20 | 1-15 |
| Surfactant | 0.5-25 | 0.5-20 | 1-15 |
| Optional ingredients | 0-25 | 0.01-20 | 0.1-20 |

TABLE 1D

Exemplary Automatic Instrument Cleaning Formulations

| | Preferred Formulation (wt. %) | More Preferred Formulation (wt. %) | Most Preferred Formulation (wt. %) |
|---|---|---|---|
| Alkali metal carbonate | 20-60 | 25-55 | 30-50 |
| Acid | 10-50 | 15-50 | 20-45 |
| Enzyme | 0.1-25 | 0.5-20 | 1-15 |
| Surfactant | 0.5-25 | 0.5-20 | 1-15 |
| Optional ingredients | 0-25 | 0.01-20 | 0.1-20 |

TABLE 1E

Exemplary Non-Instrument Formulations

| | Preferred Formulation (wt. %) | More Preferred Formulation (wt. %) | Most Preferred Formulation (wt. %) |
|---|---|---|---|
| Alkali metal carbonate | 30-75 | 35-70 | 40-70 |
| Acid | 10-40 | 12-35 | 15-30 |
| Enzyme | 0.1-15 | 0.5-10 | 1-5 |
| Surfactant | 0.1-20 | 0.5-15 | 1-10 |
| Optional ingredients | 0-25 | 0.01-20 | 0.1-20 |

The exemplary solid compositions in Tables 1A-1E are preferably dissolved to ready-to-use (RTU) compositions, which are liquid. Preferably, the dissolved RTU compositions are diluted to a concentration between about 300 ppm and about 1800 ppm. In a preferred embodiment, the exemplary solid compositions provided in Tables 1B-1D are preferably dissolved to RTU compositions, which are liquid. The RTU compositions preferably have a concentration between about 500 ppm and about 1500 ppm, more preferably between about 600 ppm and about 1250 ppm, most preferably between about 650 ppm and about 1000 ppm. In a preferred embodiment, the exemplary solid compositions provided in Table 1E are preferably dissolved to RTU compositions, which are liquid. The RTU compositions preferably have a concentration between about 300 ppm and about 1800 ppm, more preferably between about 350 ppm and about 1500 ppm, most preferably between about 400 ppm and about 1350 ppm.

Methods of Use

The solid detergent compositions described herein can be employed in a variety of cleaning methods determined by the particular cleaning application. For example, the solid detergent compositions can be employed in cleaning medical and dental instruments and/or ware.

Methods of Cleaning Medical and Dental Instruments

The solid detergent compositions can be employed in a variety of methods for cleaning, washing, or presoaking medical or dental devices, instruments, or equipment, including any of the various medical or dental instruments or devices that can benefit from cleaning with enzyme cleaning composition. Exemplary medical and dental instruments and devices include instruments, devices, tools, appliances, apparatus, and equipment used in medicine or dentistry including those than can be cold sterilized, soaked or washed and then heat sterilized, or otherwise benefit from cleaning in the disclosed compositions.

The solid detergent compositions can be used to clean medical and/or dental instruments. The medical and/or dental instruments can be soiled with blood, human tissue, or other foreign matter. A typical cycle for cleaning medical and dental instruments can have a number of different steps: pre-wash and/or presoak, wash, rinse, and drying. The pre-wash or presoak step is used to dissolve blood and other soils on the instruments and may be run with a wash solution containing detergent and possibly enzymes. The detergent compositions described herein can be used as a prewash or presoak composition. The wash part of the cycle is run with a cleaning solution; this cleaning solution can be comprised of the diluted detergent compositions described herein. Wash time, water temperature and detergent selection and concentration are typically matched according to requirements for the particular instruments and regulations in the jurisdiction. Rinses are used to remove soil dissolved in the wash stage as well as the remaining detergent. Following the rinse and/or drying step, a disinfecting step can be applied. The disinfecting step can be performed in a number of ways. Typically, a disinfecting step comprises cleaning the instrument with a sanitizer and/or at a temperature greater than about 200° F.

The methods of cleaning medical and dental instruments include diluting the solid detergent composition with water to form a cleaning solution. Preferably, the diluting step is performed at a dilution ratio of between about ⅟₃₂ oz/gal and about 1 oz/gal. The cleaning solution preferably has a diluted concentration of about 0.5 wt. % to about 85 wt. %, more preferably between about 1 wt. % and about 50 wt. %, still more preferably between about 1 wt. % and about 30 wt. %, most preferably between about 5 wt. % and about 20 wt. %.

The methods of cleaning medical and dental instruments include contacting an instrument with the cleaning solution. Preferably, the contacting step is performed at a temperature between about 50° F. and about 150° F. In an embodiment, the temperature at the contacting step is between about 50° F. and about 80° F. In an embodiment, the temperature at the contacting step is between about 90° F. and about 145° F. The blood, human tissue, and foreign matter can be removed from the instrument during the contacting step. The contacting step can be performed as a prewash or presoak step or as an automatic and/or manual wash step.

The methods of cleaning medical and dental instruments include rinsing the instrument(s) with water. In some embodiments, there is one rinse step. In some embodiments, there are two rinse steps. More rinse steps can be performed if desired. The rinsing can be performed at a temperature between about 50° F. and about 150° F. The blood, human tissue, and foreign matter can be removed from the instrument during the rinsing step.

Methods of Cleaning Ware

The compositions according to the invention can be provided as a solid. As set forth in the description of the compositions, the detergent compositions can be provided in one or more parts. Alternatively, a detergent composition may be provided in two or more parts, such that the overall detergent composition is formed in the stabilized use solution upon combination of two or more compositions. Each of these embodiments are included within the following description of the methods of the invention.

In one embodiment, the detergent compositions may be provided as a concentrate such that the detergent composition is substantially free of any added water or the concentrate may contain a nominal amount of water. The concentrate can be formulated without any water or can be provided with a relatively small amount of water in order to reduce the expense of transporting the concentrate. For example, the composition concentrate can be provided as a capsule or pellet of compressed powder, a solid, or loose powder, either contained by a water soluble material or not. In the case of providing the capsule or pellet of the composition in a material, the capsule or pellet can be introduced into a volume of water, and if present the water soluble material can solubilize, degrade, or disperse to allow contact of the composition concentrate with the water. For the purposes of this disclosure, the terms "capsule" and "pellet" are used for exemplary purposes and are not intended to limit the delivery mode of the invention to a particular shape.

In yet another embodiment, the concentrate composition can be provided in a solid form that resists crumbling or other degradation until placed into a container. Such container may either be filled with water before placing the composition concentrate into the container, or it may be filled with water after the composition concentrate is placed into the container. In either case, the solid concentrate composition dissolves, solubilizes, or otherwise disintegrates upon contact with water. In a particular embodiment, the solid concentrate composition dissolves rapidly thereby allowing the concentrate composition to become a use composition and further allowing the end user to apply the use composition to a surface in need of cleaning In another embodiment, the solid concentrate composition can be diluted through dispensing equipment whereby water is sprayed at the solid block forming the use solution. The water flow is delivered at a relatively constant rate using mechanical, electrical, or hydraulic controls and the like. The solid concentrate composition can also be diluted through dispensing equipment whereby water flows around the solid block, creating a use solution as the solid concentrate dissolves. The solid concentrate composition can also be diluted through pellet, tablet, powder and paste dispensers, and the like.

Conventional detergent dispensing equipment can be employed according to the invention. For example, commercially available detergent dispensing equipment which can be used according to the invention are available from Ecolab, Inc. Use of such dispensing equipment results in the erosion of a detergent composition by a water source to form the aqueous use solution according to the invention.

The water used to dilute the concentrate (water of dilution) can be available at the locale or site of dilution. The water of dilution may contain varying levels of hardness depending upon the locale. Service water available from various municipalities have varying levels of hardness. It is desirable to provide a concentrate that can handle the hardness levels found in the service water of various municipalities. The water of dilution that is used to dilute the concentrate can be characterized as hard water when it includes at least 1 grain hardness. It is expected that the water of dilution can include at least 5 grains hardness, at least 10 grains hardness, or at least 20 grains hardness.

The methods according to the invention are directed to cleaning a surface, such as ware in a warewash application, having numerous beneficial results, including enhancing detergency of the carbonate-based detergent composition containing stabilized enzymes, wherein the detergent composition is more effective in removing soils, preventing redeposition of the soils, and maintains low-foaming of the wash water. Preferably, the methods of cleaning a surface are performed at a temperature between about 60° F. and about 180° F., more preferably between about 80° F. and about 170° F., most preferably between about 100° F. and about 160° F.

In use, a detergent composition is applied to a surface to be washed during a washing step of a wash cycle. A wash cycle may include at least a washing step and a rinsing step and may optionally also include a pre-rinsing step. The wash cycle involves dissolving a detergent composition, which may include according to the invention. During the rinsing step, generally warm or hot water flows over the surfaces to be washed. The rinse water may include components such as, for example, surfactants or rinse aids. The detergent composition is intended for use only during the washing step of the wash cycle and is not used during the rinsing step. Preferably, the wash cycle is performed at a temperature between about 60° F. and about 180° F., more preferably between about 80° F. and about 170° F., most preferably between about 100° F. and about 160° F.

Methods of Making the Solid Detergent Compositions

The solid detergent compositions can be prepared as a cast solid, extruded solid, molded solid, a powder, or a pressed solid. The compositions can be prepared by mixing the various components together and applying the solidification process desired.

Solid block and cast solid block materials can be made by introducing into a container a castable liquid formulation of the ingredients that hardens into a solid block within a container. Preferred containers include disposable plastic containers or water soluble film containers. Other suitable packaging for the composition includes flexible bags, packets, shrink wrap, and water soluble film such as polyvinyl alcohol. In a casting process, the liquid and solid components are introduced into the final mixing system and are continuously mixed until the components form a substantially homogeneous liquid mixture in which the components are distributed throughout its mass. In an exemplary embodiment, the components are mixed in the mixing system for at least approximately 60 seconds. Once the mixing is complete, the product is transferred to a packaging container where solidification takes place. In an exemplary embodiment, the cast composition begins to harden to a solid form in between approximately 1 minute and approximately 3 hours. Particularly, the cast composition begins to harden to a solid form in between approximately 1 minute and approximately 2 hours. More particularly, the cast composition begins to harden to a solid form in between approximately 1 minute and approximately 20 minutes.

In other aspects, the solid compositions may be formed using a batch or continuous mixing system to combine ingredients. In an exemplary embodiment, a single- or twin-screw extruder is used to combine and mix one or more components at high shear to form a homogeneous mixture. In some embodiments, the processing temperature is at or below the melting temperature of the components. The processed mixture may be dispensed from the mixer by forming, casting or other suitable means, whereupon the cleaning composition hardens to a solid form. The structure of the matrix may be characterized according to its hardness, melting point, material distribution, crystal structure, and other like properties according to known methods in the art. Generally, a solid composition processed according to these methods is substantially homogeneous with regard to the distribution of ingredients throughout its mass and is dimensionally stable.

In an extrusion process, the liquid and solid components are introduced into final mixing system and are continuously mixed until the components form a substantially homogeneous semi-solid mixture in which the components are distributed throughout its mass. The mixture is then discharged from the mixing system into, or through, a die or other shaping means. The product is then packaged. In an exemplary embodiment, the formed composition begins to harden to a solid form in between approximately 1 minute and approximately 3 hours. Particularly, the formed composition begins to harden to a solid form in between approximately 1 minute and approximately 2 hours. More particularly, the formed composition begins to harden to a solid form in between approximately 1 minute and approximately 20 minutes.

In a pressed solid process, a flowable solid, such as granular solids or other particle solids are combined under pressure to form the solid composition. In a pressed solid process, flowable solids of the compositions are placed into a form (e.g. a mold or container). The method can include gently pressing the flowable solid in the form to produce the solid cleaning composition. Pressure may be applied by a block machine or a turntable press, or the like. Pressure may be applied at about 1 to about 3000 psi, about 1 to about 2000 psi, about 1 to about 1000 psi, about 1 to about 500 psi, about 1 to about 300 psi, about 5 psi to about 200 psi, or about 10 psi to about 100 psi. In certain embodiments, the methods can employ pressures as low as greater than or equal to about 1 psi, greater than or equal to about 2, greater than or equal to about 5 psi, or greater than or equal to about 10 psi. As used herein, the term "psi" or "pounds per square inch" refers to the actual pressure applied to the flowable solid being pressed and does not refer to the gauge or hydraulic pressure measured at a point in the apparatus doing the pressing.

The methods can optionally include a curing step to produce the solid compositions. As referred to herein, an uncured composition including the flowable solid is compressed to provide sufficient surface contact between particles making up the flowable solid that the uncured composition will solidify into a stable solid composition. A sufficient quantity of particles (e.g. granules) in contact with one another provides a binding of particles effective for making a stable solid composition. A curing step may be included, allowing the pressed solid to solidify for a period of time, such as a few hours, or about 1 day (or longer). In additional aspects, the methods could include vibrating the flowable solid in the form or mold, such as the methods disclosed in U.S. Pat. No. 8,889,048, which is herein incorporated by reference in its entirety.

The use of pressed solids provides numerous benefits over conventional solid block or tablet compositions, which can require high pressure in a tablet press, or casting requiring the melting of a composition consuming significant amounts of energy, and/or extrusion requiring expensive equipment and advanced technical expertise. Pressed solids overcome the various limitations of other solid formulations for which there is a need for making solid compositions. Moreover, pressed solid compositions retain their shape under conditions where the compositions may be stored or handled.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The following Examples provide exemplary embodiments of the solid, neutral, enzyme detergent compositions of the present application that provide improved stability and cleaning performance as well as reduced packaging costs. These compositions may further be utilized in an automatic washer/disinfector or manually in a sink, and The following materials were employed:

Sodium Carbonate, an exemplary alkali metal carbonate available from multiple commercial sources;

Adipic Acid, an exemplary polycarboxylic acid available from multiple commercial sources;

An aminocarboxylate was employed as an exemplary commercially available from water conditioning agent;

Acusol 445 and 445ND are acrylic acid polymers, exemplary water conditioning agents available from Dow Chemical Company;

Acusol 448 is an acrylic acid/maleic acid co-polymer, an exemplary water conditioning agent available from Dow Chemical Company;

Exemplary commercially available proteases mainly derived from subtisilin A were employed.

Exemplary commercially available fatty alcohol polyglycol ethers having a C8-C12 alcohol carbon chain length were employed.

An exemplary commercially available amine oxide surfactant was employed.

An exemplary commercially available surfactant having (PO)(EO)(PO) structure, an average molecular weight of less than 3000 g/mole, and a cloud point of 46° C. at 1 wt. % concentration in an aqueous solution;

An exemplary preservative derived from isothiazolinone was employed.

Example 1

In this Example, exemplary formulations according to the present application were prepared to evaluate their overall stability in block and powder form. 27 exemplary formulations were prepared as described in Table 2 below. The exemplary formulations had a solid matrix holding 10-15% liquid composition and produced a pH of about 8-9 in solution. Observations regarding the stability of these formulations are provided in Table 3 below.

TABLE 2

| Material (grams) | Formulation | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Sodium carbonate Dense ash | 20.5 | 10.5 | 8 | 8 | | | | 50 | 16 | | 8 | 21.6 | 55 |
| Sodium bicarbonate, powder | 65 | 75 | 58 | | | | | | | | 60 | | |
| Sodium bicarbonate, granular | | | | | 58 | | | | 52 | | | 43.4 | |
| Sodium acetate | | | | | | | | | | | | | |
| CMC-7LT | | | | 20 | 20 | 20 | 20 | | | 10 | | 10 | |
| Liquinase evity | 10 | 10 | 10 | 10 | 10 | 10 | 10 | 10 | 10 | 10 | 10 | 10 | 10 |
| PEG 4000 | | | | | | | | | | 30 | | | |
| Acusol 445ND | 5 | 5 | 5 | 5 | 5 | 5 | 30 | 5 | | | | | |
| Urea, microprilled | | | | | 65 | | 60 | | | | | | |
| Sodium chloride | | | | | | 65 | | | | | | | |
| SXS, 96% | | | | | | | | | | | | 60 | 20 |

TABLE 2-continued

| Material | | | | | | | | | | | |
|---|---|---|---|---|---|---|---|---|---|---|---|
| Malic acid | | | | | | | | | | | |
| Citric acid | | | | | | | | | | 15 | 16 |
| Glutamic acid | | | | | | | | | | 21.6 | 55 |
| Maleic acid | | | | | | | | | | | |
| EDTA, acid | | | | | | 35 | 15 | | | | |

| Material (grams) | Formulation | | | | | | | | | | |
|---|---|---|---|---|---|---|---|---|---|---|---|
|  | 14 | 15 | 16 | 17 | 18 | 19 | 20 | 21 | 22 | 23 | 24 |
| Sodium carbonate | 55 | 55 | 25 | 25 | 25 | 25 | | 55 | | 27.5 | 22.5 |
| Dense ash | | | | | | | | | 55 | 27.5 | 22.5 |
| Sodium bicarbonate, powder | | | | 50 | | | | | | | |
| Sodium bicarbonate, granular | | | 50 | | 40 | 20 | | | | | |
| Sodium acetate | | | | | 10 | 30 | 90 | | | | |
| CMC-7LT | | | | | | | | | | | |
| Exemplary protease | 10 | 10 | 10 | 10 | 10 | 10 | 10 | 10 | 10 | 10 | 10 |
| PEG 4000 | | | | | | | | | | | |
| Acusol 445ND | | | | | | | | | | | |
| Urea, microprilled | | | | | | | | | | | |
| Sodium chloride | | | | | | | | | | | |
| SXS, 96% | | | | | | | | | | | |
| Malic acid | | 35 | | | | | | | | | |
| Citric acid | 35 | | | | | | | | | | |
| Glutamic acid | | | | | | | | 35 | 35 | 35 | 35 |
| Maleic acid | | | | | | | | | | | |
| EDTA, acid | | | 15 | 15 | 15 | 15 | | | | | |

TABLE 3

| | Observations | |
|---|---|---|
| Formulation | Block | Powder |
| 1 | No cracking. | Moist powder, small particle, could cause flow issues |
| 2 | No cracking, but brittle block | Moist powder, small particle size could cause flow issues |
| 3 | No cracking, less friable than formulations 1-2 | More flowable powder than formulations 1-2 |
| 4 | No cracking, less friable than formulations 1-3 | More flowable than formulations 1-3 |
| 5 | Very hard block, not friable | Wet powder, larger particle size |
| 6 | Hard block, not friable | Wet and sticky powder, poor flow |
| 7 | Did not press, too wet | Very wet powder, did not press |
| 8 | Very hard block, best block of all runs | Very flowable powder |
| 9 | Hard block, not as good as 8 | Flowable powder, better than 1-7 but not as good as 8 |
| 10 | Extremely soft and wet block, cracks on blocks | Wet tacky powder, small particle size causes flow issues |
| 11 | Harder than 10 but still soft compared to 1-9 | Wet powder |
| 12 | Pressed nice hard blocks | Flowable powder but not as good as all light ash/acid formulas; vigorous reaction when diluted |
| 13 | Pressed hard blocks, nice | Dry powder, minor reaction when mixing, major reaction when diluted |
| 14 | | |
| 15 | Horizontal cracks on block | Free-flowing powder, minor reaction when mixing, major reaction when diluted |
| 16 | | Better than 20 but still wet powder with poor flow |
| 17 | | Fairly wet powder with poor flow; tacky |
| 18 | | Improved over 19 and 20, but may still be too wet |
| 19 | | Better flow than 19-21 but the small particle size has poor flow |

TABLE 3-continued

| | Observations | |
|---|---|---|
| Formulation | Block | Powder |
| 20 | | Same as 22 |
| 21 | Very hard blocks, no cracks | Free flowing powder, small particle size may decrease flow |
| 22 | Very hard blocks, no cracks | More wet but large size of dense ash helps flow some |
| 23 | Very hard blocks, no cracks | Better flow than 21 and 22 |
| 24 | Very hard blocks, no cracks | Good flow, dries out/hydrates with time |

Overall the exemplary formulations demonstrated the ability to form a solid block and/or powder, with the exception of formulation 7. In particular, exemplary formulations 1-4, 8-9, and 24-27 demonstrated significantly improved stability and flow in both solid block and solid powder states.

Example 2

In this Example, further exemplary formulations according to the present application were prepared to evaluate their overall stability in block form, in powder form, and when the compositions were dispensed into a 10% sump solution. 8 exemplary formulations were prepared as described in Table 4 below. The exemplary formulations had a solid matrix holding 10-15% liquid composition and produced a pH of about 8-9 when dispensed into a 10% sump solution. Blocks were held at 122° F. for four weeks, and their swelling was measured periodically. 10% sump solutions were held at room temperature (RT) and at 122° F. and were checked for phase separation immediately and again after 24 hours. These observations are provided in Table 5 below.

TABLE 4

| | Exemplary Formulations | | | | | | | |
|---|---|---|---|---|---|---|---|---|
| Material (grams) | 1 | 2 | 3 | 4 | 5 | 6 | 7 | 8 |
| Sodium carbonate, light | 50 | 22.5 | 50 | 50 | 45 | 45 | 18.75 | 42.5 |
| Sodium carbonate, dense | | 22.5 | | | | | 18.75 | |
| Exemplary protease | 10 | 10 | 10 | 10 | 10 | 10 | 10 | 10 |
| Acusol 445ND | | 5 | 5 | 5 | 5 | 5 | 5 | 5 |
| DP5005 | 5 | | | | | | | |
| Genapol EP2564 | 5 | | 5 | | | 2.5 | 5 | 5 |
| Lutensol AT25 | | | | | 5 | 5 | 5 | 5 |
| Glutamic acid | | 45 | | | 45 | | 37.5 | |
| EDTA, acid | 35 | | 35 | 35 | | 32.5 | | 32.5 |

TABLE 5

| | Observations | | |
|---|---|---|---|
| Formulation | Block | Powder | Separation |
| 1 | Soft tablet out of press, solidified over time, minor horizontal crack | Damp powder, may have flow issues through all fill and chutes | Yes, separated at room temperature |
| 2 | Softer block out of press than version w/no surfactant; hard in a few minutes | Damp powder, may have flow issues through all fill and chutes | No separation at RT |
| 3 | Harder block than formulation 1, but not as hard as without surfactant | Damp powder, may have flow issues through all fill and chutes | Yes, separated at room temperature |
| 4 | About the same as formulation 3, maybe a little harder | Damp powder, may have flow issues through all fill and chutes | No separation at RT |
| 5 | Very hard block right out of press, no liquid surfactant | Very free flowing powder; best of all formulas, should be good in press system | No separation at room temperature or at 122° F. |
| 6 | Similar to blocks 3-4, no cracks, holds together, very hard after 5 minutes | Damp powder, may have flow issues through all fill and chutes | No separation at room temperature or at 122° F. |
| 7 | Similar to block 6, no cracks, holds together, very hard after 5 minutes | Damp powder, may have flow issues through all fill and chutes | No separation at room temperature or at 122° F. |
| 8 | Similar to block 6, no cracks, holds together, very hard after 5 minutes | Damp powder, may have flow issues through all fill and chutes | No separation at room temperature or at 122° F. |

Formulations 2 and 4-8 formed solid blocks and powder, and 10% sump solutions of these formulations did not separate at room temperature. In particular, 10% sump solutions of formulations 5-8 demonstrated surprising stability and did not separate even at 122° F. The blocks' dimensional stability in terms of width and height was further assessed over the course of four weeks. The formulations of the present application demonstrate superior dimensional stability, swelling less than 3% over four weeks at room temperature, 104° F. and 122° F. The results are displayed in FIGS. 2A and 2B.

Figure 2A:
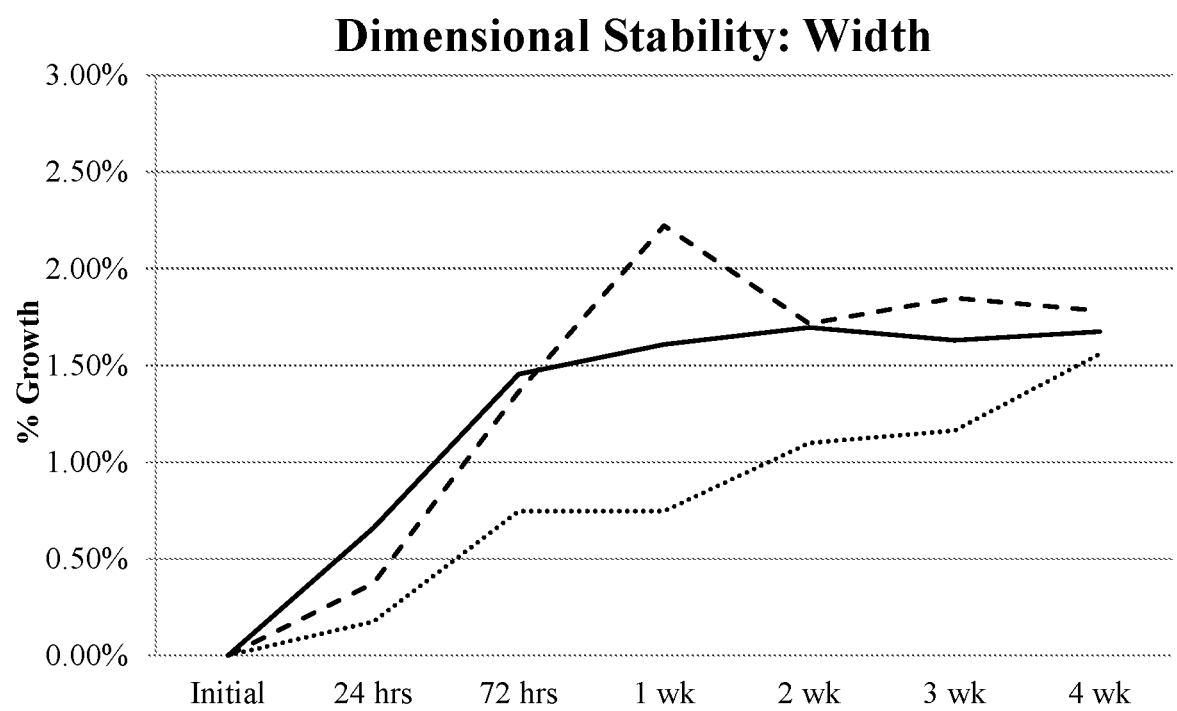
FIG. 2A is a graph showing the dimensional stability based on percent growth of the width of exemplary solid enzymatic detergent tablets.
Figure 2B:
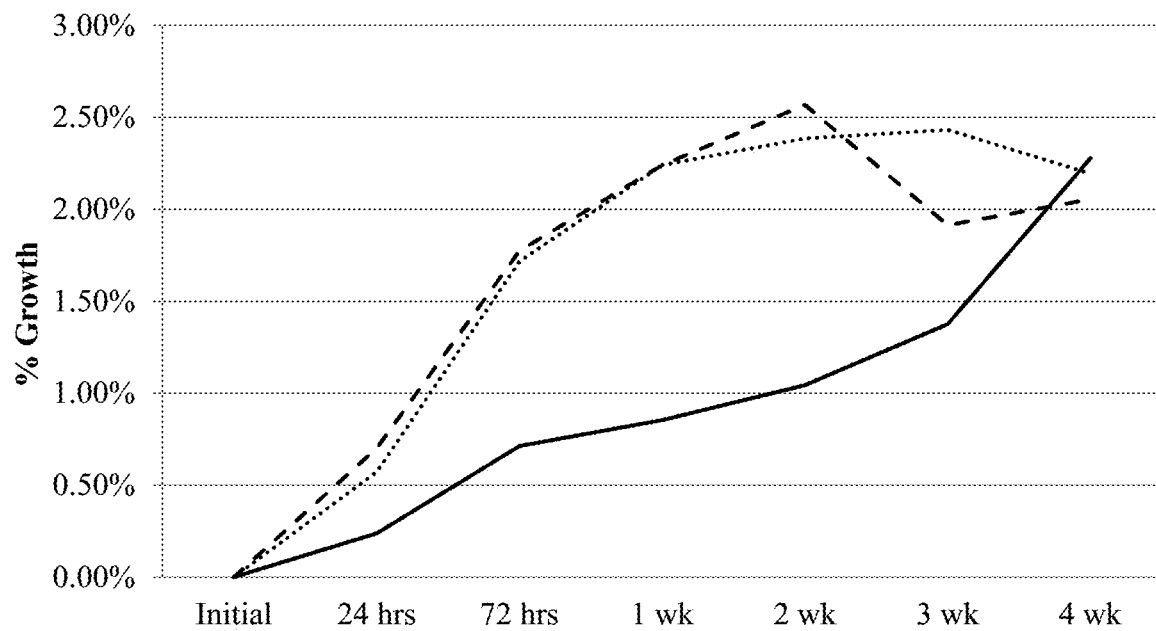
FIG. 2B is a graph showing the dimensional stability based on percent growth of the height of exemplary solid enzymatic detergent tablets.
Figure 3A:
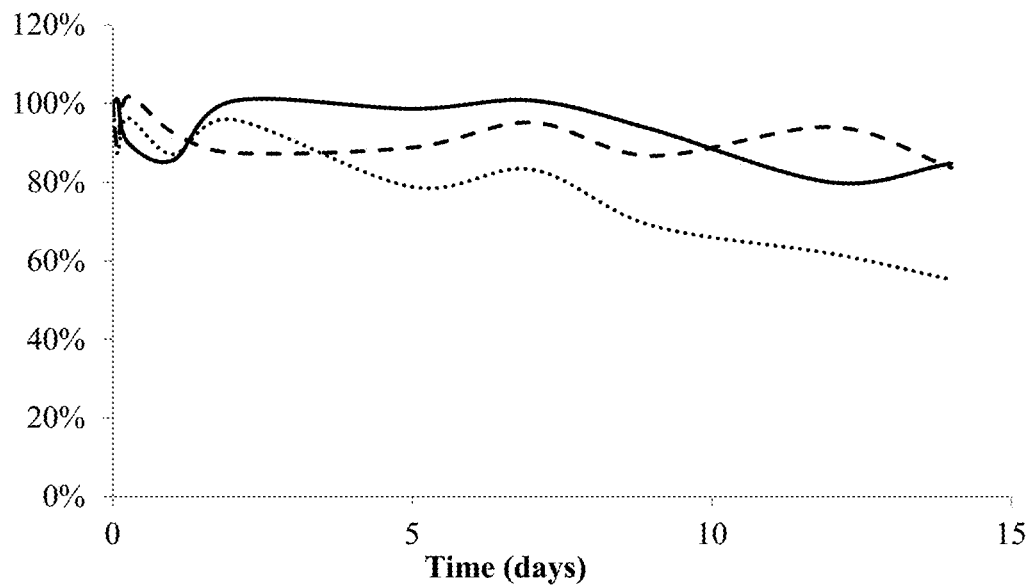
FIGS. 3A-3E are graphs of enzyme stability data for the compositions prepared and tested in Example 4 over fourteen das at room temperature, 40° C., and 50° C.
Figure 3B:
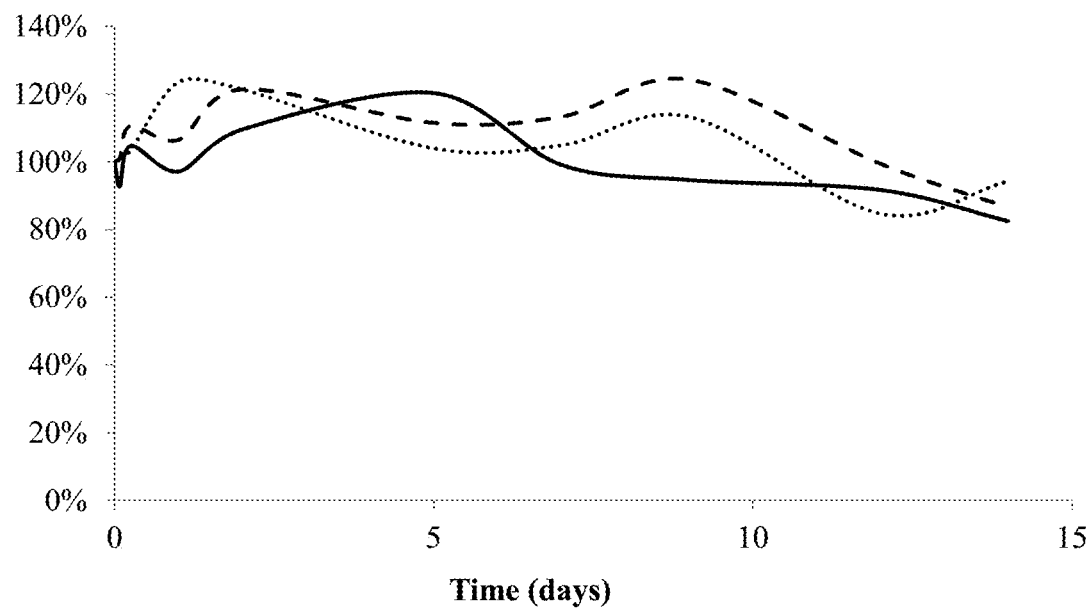
Figure 3C:
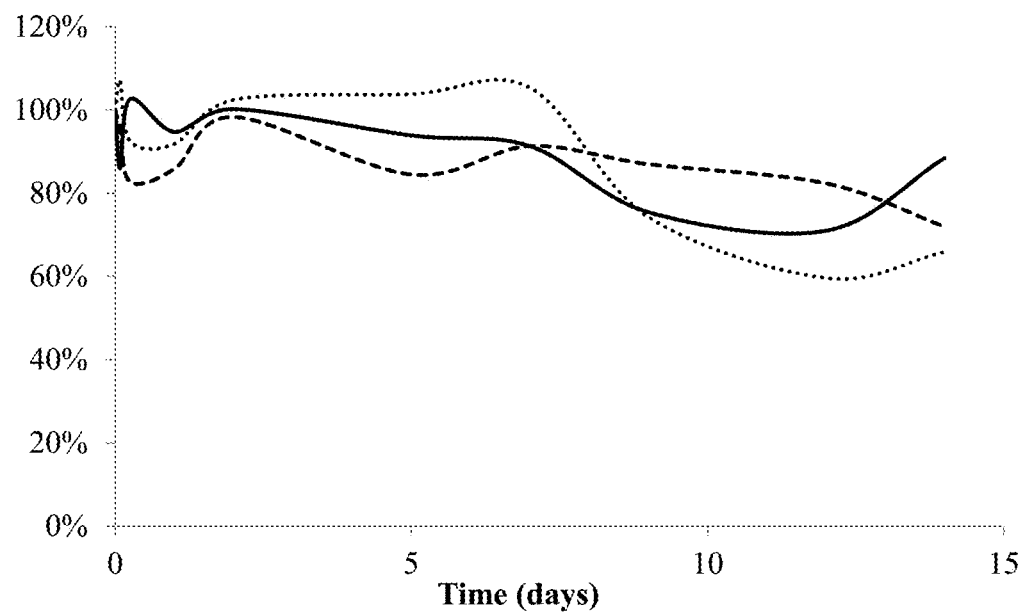
Figure 3D:
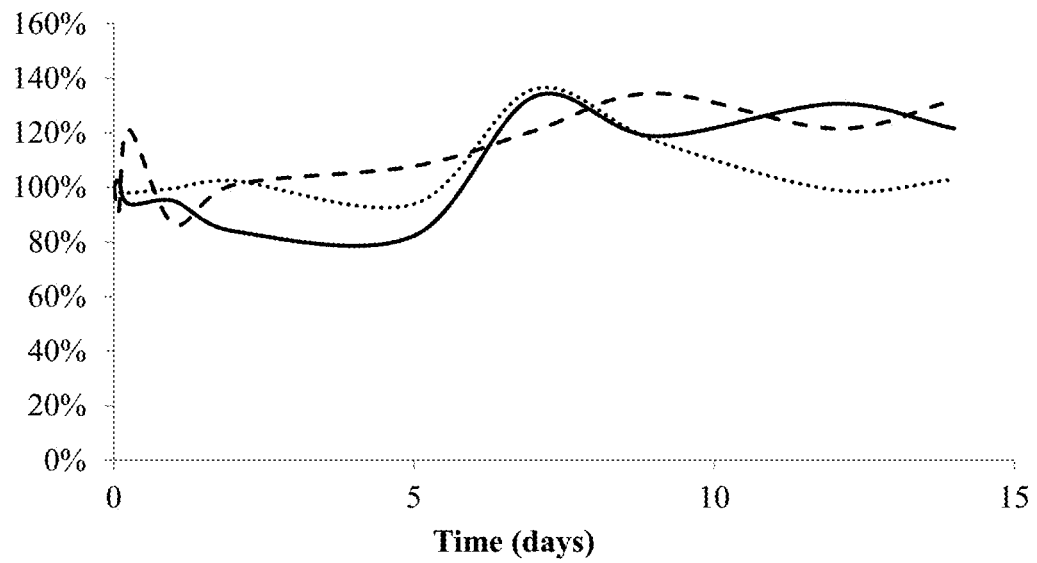
Figure 3E:
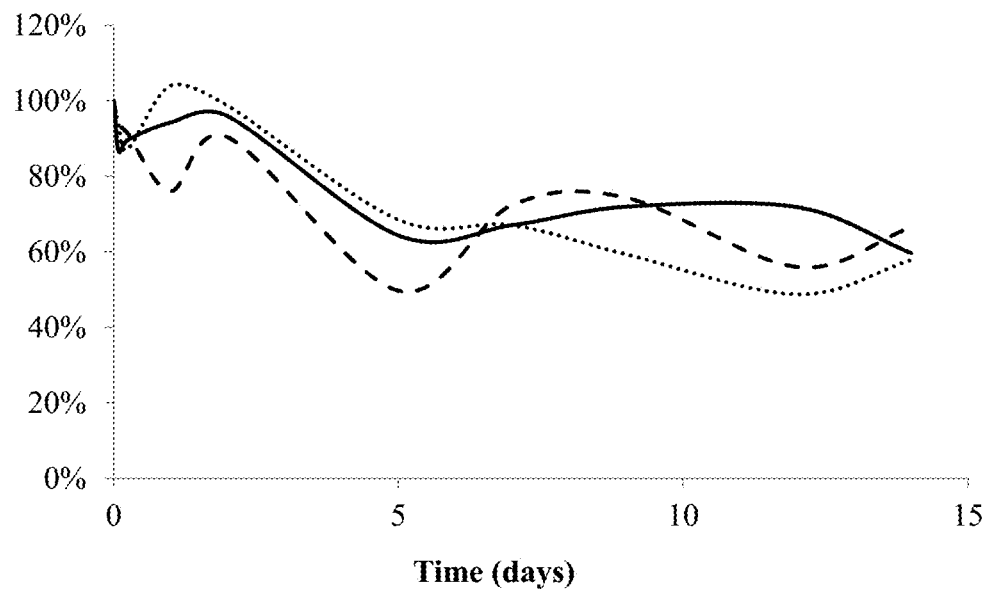

In FIG. 2A, the solid line reflects the average percent growth in width of the solid blocks kept at 122° F., the long-hashed line represents the average percent growth in width of the solid blocks kept at 104° F., and the dotted line represents the average percent growth in width of the solid blocks kept at room temp. As can be seen in FIG. 2A the blocks had less than 2.00% growth in width after 4 weeks of storage. In FIG. 2B, the solid line reflects the average percent growth in width of the solid blocks kept at room temperature, the long-hashed line represents the average percent growth in width of the solid blocks kept at 122° F., and the dotted line represents the average percent growth in width of the solid blocks kept at 104° F. As can be seen in FIG. 2B the blocks had less than 2.50% growth in height after 4 weeks of storage.

Example 3

In this Example, exemplary formulations according to the present application were prepared to determine their foam profiles. The formulations had a common formula as provided in Table 6 with differing surfactants species which are reflected in Table 7. The formulations were evaluated using a Glewwe foam apparatus. For each formulation, three liters of a 660-ppm detergent solution were prepared in the Glewwe foam apparatus, and heated to 122° F. (50° C.) using a steam jacket. A ruler was attached to the side of the apparatus, and the solution was level with the bottom of the ruler. The pump was turned on, recirculating the solution through a nozzle at 6 psi and generating foam. After 60 seconds of recirculation, the pump was turned off and foam height of the foam was recorded 0, 15, and 60 seconds after pump shutoff. Stable foam remains for several minutes after agitation is stopped. Partially stable foam breaks slowly, within a minute. Unstable foam breaks rapidly, in less than 15 seconds.

The cloud point of a 10% sump solution of each formulation was also recorded. Cloud point is generally defined as the temperature at which a particular concentration of surfactant becomes insoluble. It was determined that a cloud point of less than 26° C. is incompatible with conditions in certain methods of use. Thus, if a surfactant was determined to have a cloud point of less than 26° C., it was excluded from testing. A surfactant can function to defoam the composition when used at temperatures at or above this cloud point. The results are depicted in Table 7 below.

TABLE 6

| Material | Exemplary Solid Formulation 1 (wt. %) |
| --- | --- |
| Acrylic Acid Polymer | 8 |
| Adipic Acid | 29.5 |
| Alkali Metal Carbonate | 33 |
| Amino Carboxylate | 14 |
| Exemplary protease | 10 |
| Preservative | 0.5 |
| Surfactant | 5 |
| Water | — |

TABLE 7

| Surfactant | Cloud Point (° C.) | Foam @ 50° C. | | |
| --- | --- | --- | --- | --- |
| | | 0 sec | 15 sec | 60 sec |
| PO-EO-PO surfactant A, MW = 1950 g/mol, CP (1% aq.) = 69° C. | >40 | 3.5 | 0.25 | 0.125 |
| PO-EO-PO surfactant B, MW = 2650 g/mol, CP (1% aq.) = 46° C. | 28.5 | 0.75 | 0 | 0 |
| 2:3 PO-EO-PO surfactant A:PO-EO-PO surfactant B | 30 | 1 | 0 | 0 |
| 1:3 PO-EO-PO surfactant A:PO-EO-PO surfactant B | 29 | 1 | 0 | 0 |
| Caprylamidopropyl betaine | >40 | 0 | 0 | 0 |
| 12:1 caprylamidopropyl betaine:disodium alkyl hydroxypropyl iminodipropionate | >40 | 0 | 0 | 0 |

Several surfactants illustrate ideal low foam profiles in a solid composition. (Table 7). In particular, PO-EO-PO surfactants provide a low foam profile or no foam at 50° C. at a preferable cloud point.

Example 4

Several formulations according to the present application were prepared according to Table 8 below. These formulations were evaluated to determine the stability of the enzyme over 14 days at room temperature, at 40° C., and at 50° C. The enzyme stability data for each of the exemplary formulations are depicted in FIGS. 3A through 3E where room temperature is represented by the solid line, 40° C. is represented by hashed lines, and 50° C. is represented by dotted lines. Surprisingly, the enzyme stability showed little to no degradation even at elevated temperatures.

TABLE 8

| Material (wt. %) | Exemplary Formulations | | | | |
| --- | --- | --- | --- | --- | --- |
| | 1 | 2 | 3 | 4 | 5 |
| Sodium Carbonate | 25 | 25 | 36.5 | 47.5 | 25 |
| Adipic acid | 15 | 15 | | | 15 |
| Glutamic acid | | | 43.5 | | |
| Acid EDTA | | | | 32.5 | |
| Exemplary protease | 10 | 10 | 10 | 10 | 10 |
| Tetronic 90R4 | 5 | 5 | 5 | 5 | |
| Acusol 445ND | 45 | 5 | 5 | 5 | 5 |
| Sodium Gluconate | | 40 | | | 40 |
| Water | | | | | 5 |

Example 5

TOSI coupons (Test Object Surgical Instruments) are commercially available test substrates that are comprised of stainless steel coupons soiled with dried blood and a fibrin source. The TOSI is made in a quality-controlled environment (ISO certified facility), ensuring consistency among individual tests. The extent to which solid detergent compositions can remove soil from TOSIs generally represents the efficacy of the detergent compositions.

The Steris Verify Indicatoris an indicator that provides an assessment of the performance of an automated washer-disinfector and an instrument cleaning chemistry. The indicator contains a formulation (comprising a proprietary protein, lipid, and polysaccharide) dried on the two sides of a plastic carrier, mimicking soiling on a surface. The indicator has a "L" shape, exposing four surfaces to be cleaned, and creating a realistic cleaning-disinfecting challenge. Steris Verify Indicators are commercially available from Steris.

The Wash Check is a commercially available indicator used to monitor several variables during the cleaning process in a washer/disinfector. The indicator is comprised of a thin metal coupon soiled with a clinically relevant soil used in conjunction with the cleaning monitor holder that blocks half of the soiled area to simulate the impact of mechanical agitation and detergent contact with one coupon.

The Ecolab Washer Disinfector Process Indicator provides feedback on the washer/disinfector process and the impact of several variables throughout the wash step. The indicators are comprised of a clinically relevant soil (comprising a proprietary blend of proteins, lipids, and polysaccharides) on a thin plastic coupon. These are used in conjunction with the Ecolab Washer Disinfector Holder to evaluate several variables in the wash process. Ecolab Washer Disinfector Process Indicators are commercially available from Ecolab.

Apparatus and Materials
Six TOSIs
Steris Automatic Washer-Disinfector (3 Levels)
Three Wash Checks
One Verify indicator
Ecolab Washer Disinfector Process Indicator ("WDPI")

Three instrument trays were placed in a staggered arrangement on the three levels of the Steris Automatic Washer-Disinfector. Two TOSIs were placed in each instrument tray. A WDPI was placed on the middle level in an instrument tray. FIG. 1 depicts the arrangement of the instrument trays in the Washer-Disinfector.

After loading the indicators as described, the washer doors were closed, and the appropriate wash cycle and detergent concentration were selected. The wash cycle, using 5 grain water, consisted of three parts: (1) a pre-rinse in cold water, (2) a wash cycle at either 110° F. or 122° F. with the detergent present at a concentration of 1/20 oz/gal, 3/8 oz/gal or 1/2 oz/gal, and (3) a rinse and drain with hot water.

In this Example, the first two steps of the wash cycle were run, and the wash was cancelled during the two-minute rinse and drain step. The total length of the wash cycles ranged between about 5 to about 7 minutes. Upon cancellation of the wash cycle, the washer doors were opened, and the indicators were immediately removed. The Verify indicator and TOSIs were set on their sides to dry. The Verify indicator and TOSIs were rated after completely dry.

An exemplary formulation was prepared to demonstrate the efficacy of the compositions of the present invention. The exemplary formulation was prepared as shown in Table 11 below. This exemplary formulation was tested against three comparative formulations (exemplary of commercially existing products). Comparative Formulation A corresponds to Prolystica Ultra Concentrate HP Enzymatic Cleaner, available from Steris. Comparative Formulation B corresponds to Endozime AW Triple Plus, available from Ruhof. Finally, Comparative Formulation C corresponds to Power-Con Triple Enzyme Detergent Concentrate, available from Getinge. The comparative formulations were evaluated per the product label instructions for use regarding detergent concentrations. The formulations were evaluated in wash cycles that were 5 or 7 minutes, and 110° F. and 122° F. as illustrated in Tables 9 and 10, respectively. The extent of soil/residue removal was ranked according to the following scale:

| Soil and Residue Removal Scale |
|---|
| TOSI |
| 1 = no residue |
| 1.5 = residue when looking close/carefully; hard to see |
| 2 = very small amount of residue; visible at first look |
| 3 = multiple spots of residue; more than small amount residue |
| Wash Check |
| 1 = no red |
| 2 = red when at an angle; no red straight on |
| 3 = red when looking straight on and at angle |
| Verify |
| 1 = no red |
| 1.5 = red on top half; no red on bottom half |
| 2 = red on edges or very small amount of red anywhere |
| 3 = red on more than edges |
| WDPI |
| 1 = no red |
| 2 = some faint red; no dark red |
| 3 = any amount of dark red |

TABLE 9

Automatic Washer-Disinfector Test at 110° F.

| Test | Rack place | Comparative Form. A, 1/20 oz/gal | | | Comparative Form. B, 3/8 oz/gal | | Comparative Form. C, 1/2 oz/gal | Exemplary Form. 1, 1/20 oz/gal | | |
|---|---|---|---|---|---|---|---|---|---|---|
| | | Run 1 | Run 2 | Run 3 | Run 1 | Run 2 | Run 1 | Run 1 | Run 2 | Run 3 |
| TOSI | Top Right | 1 | 1 | 1 | 1 | 2 | 1 | 1 | 1 | 1.5 |
| | Top Left | 1 | 2 | 2 | 1 | 3 | 1 | 1 | 1 | 2 |
| | Middle Right | 1.5 | 1 | 2 | 2 | 1 | 2 | 2 | 1 | 2 |
| | Middle Left | 1.5 | 1 | 2 | 2 | 2 | 2 | 1 | 1 | 2 |

TABLE 9-continued

Automatic Washer-Disinfector Test at 110° F.

| Test | Rack place | Comparative Form. A, 1/20 oz/gal | | | Comparative Form. B, 3/8 oz/gal | | Comparative Form. C, 1/2 oz/gal | Exemplary Form. 1, 1/20 oz/gal | | |
|---|---|---|---|---|---|---|---|---|---|---|
| | | Run 1 | Run 2 | Run 3 | Run 1 | Run 2 | Run 1 | Run 1 | Run 2 | Run 3 |
| | Bottom Right | 1 | 1 | 1 | 1 | 2 | 1 | 1 | 1 | 1 |
| | Bottom Left | 1 | 1 | 1.5 | 1.5 | 3 | 1.5 | 1.5 | 1 | 1 |
| Wash Check | Top Right | 2 | 2 | 1 | 2 | 2 | 2 | 1 | 1 | 2 |
| | Middle Right | 2 | 2 | 2 | 2 | 2 | 2 | 1 | 1 | 2 |
| | Bottom Left | 2 | 2 | 2 | 2 | 3 | 2 | 1 | 1 | 2 |
| Verify | Middle Left | N/A | 1 | N/A | 2 | N/A | 2 | 1 | 1 | 1 |
| WDPI | Middle Left | N/A | 3 | N/A | 3 | N/A | 3 | 1 | N/A | 1 |

TABLE 10

Automatic Washer-Disinfector Test at 122° F.

| Test | Rack position | Exemplary Form. 1, 1/20 oz/gal | | | Comparative Form. B, 3/8 oz/gal | Comparative Form. C, 1/2 oz/gal |
|---|---|---|---|---|---|---|
| | | Run 1 | Run 2 | Run 3 | Run 1 | Run 2 |
| TOSI | Top Right | 1 | 1 | 1 | 2 | 1 |
| | Top Left | 1 | 1 | 1 | 3 | 3 |
| | Middle Right | 2 | 1 | 1 | 2 | 1.5 |
| | Middle Left | 1 | 1 | 1 | 2 | 1 |
| | Bottom Right | 1.5 | 1 | 1 | 1 | 1 |
| | Bottom Left | 1.5 | 2 | 1 | 2 | 1.5 |
| Wash Check | Top Right | 1 | 2 | 2 | 1 | 1 |
| | Middle Right | 1 | 2 | 1 | 1 | 1 |
| | Bottom Left | 2 | 2 | 1 | 1 | 1 |
| Verify | Middle Left | 1 | N/A | 1 | N/A | N/A |
| WDPI | Middle Left | 1 | N/A | N/A | 3 | 2 |

The formulations of the present application demonstrated similar or improved soil and residue removal as compared to the three comparative formulations. The exemplary formulations maintained this elevated level of efficacy on varying surfaces, and at variable temperatures.

Example 6

In this Example, a further exemplary formulation of the present application was evaluated using the same procedures as Example 5. The formulation was prepared according to Table 11, and the resulting data are provided in Tables 12-15 below. In evaluating the soil and residue removal, the following scale was used:

Soil and Residue Removal Scale

6 = completely clean, no residue or stain
12 = almost completely clean, very small amount of residue
18 = multiple spots of residue, more than a small amount of soil remaining

TABLE 11

| Material (wt %) | Exemplary Formulation |
|---|---|
| Acusol 445 ND | 8 |
| Adipic Acid | 29.25 |
| Sodium Carbonate | 32.75 |
| Exemplary protease | 10 |
| Neolone M-10 | 1 |
| Trilon M | 14 |
| PO-EO-PO surfactant, MW = 2650 g/mol, CP (1% aq.) = 46° C. | 5 |

TABLE 12

Wash Cycle 5-6 Minutes, 110° F.

| Product | 5 min | 5 min | 6 min | 6 min | 6 min | 6 min | 6 min | 6 min |
|---|---|---|---|---|---|---|---|---|
| TOSI | 8 | 7.5 | 7.5 | 6 | 9.5 | 11.5 | 7 | 9 |
| Wash Check | 6 | 6 | 6 | 6 | 12 | 6 | N/A | 6 |
| Verify | 6 | 6 | 6 | 6 | 6 | N/A | N/A | N/A |
| WDPI | 6 | N/A | 6 | N/A | 6 | 6 | N/A | N/A |

TABLE 13

Wash Cycle 7-10 Minutes, 110° F.

| Product | 7 min | 7 min | 7 min | 7 min | 8 min | 10 min |
|---|---|---|---|---|---|---|
| TOSI | 10 | 6.5 | 6 | 6.5 | 6 | 6 |
| Wash Check | N/A | N/A | 6 | 6 | 6 | 6 |
| Verify | N/A | N/A | N/A | 6 | 6 | 6 |
| WDPI | N/A | N/A | N/A | N/A | N/A | N/A |

TABLE 14

Trial No. (Wash Cycle 6 Minutes, 122° F.)

| Product | 1 | 2 | 3 | 4 | 5 | 6 |
|---|---|---|---|---|---|---|
| TOSI | 11 | 8 | 7 | 10 | 11 | 6 |
| Wash Check | 6 | 8 | 12 | N/A | 6 | 8 |

TABLE 14-continued

| | Trial No. (Wash Cycle 6 Minutes, 122° F.) | | | | | |
|---|---|---|---|---|---|---|
| Product | 1 | 2 | 3 | 4 | 5 | 6 |
| Verify | 6 | 6 | N/A | N/A | N/A | 6 |
| WDPI | N/A | 6 | N/A | N/A | N/A | N/A |

TABLE 15

| | Wash Cycle 7-10 Minutes, 122° F. | | |
|---|---|---|---|
| Product | 7 min | 8 min | 10 min |
| TOSI | 6.5 | 7 | 6 |
| Wash Check | 6 | 6 | 6 |
| Verify | 6 | 6 | 6 |
| WDPI | N/A | N/A | N/A |

The exemplary composition provides superior soil and residue removal on a variety of surfaces. (Tables 12-15). Further, the compositions removed soil and residue at varying lengths of wash cycles and varying temperatures. (Tables 12-15).

Example 7

In this Example, commercially available detergents were evaluated using the same procedures as Example 5. The results were then used to compare the formulations of the present application as described in Example 6 with compositions already available. As in Example 5, Comparative Formulation A corresponds to Prolystica Ultra Concentrate HP Enzymatic Cleaner, available from Steris. Comparative Formulation B corresponds to Endozime AW Triple Plus, available from Ruhof. Finally, Comparative Formulation C corresponds to PowerCon Triple Enzyme Detergent Concentrate, available from Getinge. The comparative formulations were evaluated per the product label instructions for use regarding detergent concentrations, wash cycle lengths, and temperatures, each of which are indicated in the tables. Further, the soil evaluation scale as described in Example 6 was used to evaluate the efficacy of the compositions. The resulting data are provided in Tables 16-18 below.

TABLE 16

| | Comparative Formulation A (Wash Cycle 6 Minutes, 110° F.) | | | | | |
|---|---|---|---|---|---|---|
| Product | 1/20 oz/gal 1 | 1/20 oz/gal 2 | 1/40 oz/gal 3 | 1/20 oz/gal 4 | 1/20 oz/gal 5 | 1/40 oz/gal 6 |
| TOSI | 7 | 7 | 12 | 9.5 | 7 | 8 |
| Wash Check | 12 | 12 | 12 | 10 | 12 | N/A |
| Verify | N/A | 6 | N/A | N/A | N/A | N/A |
| WDPI | N/A | 18 | 18 | N/A | N/A | N/A |

TABLE 17

| | Comparative Formulation B (Wash Cycle 6 Minutes) | | | |
|---|---|---|---|---|
| Product | 110° F. 3/8 oz/gal 1 | 110° F. 3/8 oz/gal 2 | 122° F. 3/8 oz/gal 3 | 110° F. 1/2 oz/gal 4 |
| TOSI | 8.5 | 13 | 12 | 9.5 |
| Wash Check | 12 | 14 | 6 | 6 |
| Verify | 12 | N/A | N/A | N/A |
| WDPI | 18 | N/A | 18 | N/A |

TABLE 18

| | Comparative Formulation C (Wash Cycle 6 Minutes, 122° F., 1/2 oz/gal) | |
|---|---|---|
| Product | 1 | 2 |
| TOSI | 7.5 | 9 |
| Wash Check | 12 | 6 |
| Verify | 6 | N/A |
| WDPI | 18 | 12 |

Overall the comparative formulations were less able to remove soil and residue on the variety of evaluated surfaces. The comparative formulations consistently left at least some residue behind after a wash. In comparison, the formulations of the present application demonstrated surprising efficacy in removing residue and soil from the same instruments under similar conditions.

Example 8

Testing was performed to evaluate the efficacy of the exemplary manual instrument solid enzymatic detergents at removing simulated surgical soil. For this testing an exemplary manual instrument solid enzymatic detergent was prepared according to Table 19 and tested against two exemplary commercially available detergents by soaking a TOSI indicator in RTU solutions of the detergents.

TABLE 19

| Material | Wt. % |
|---|---|
| Acusol 445 ND | 8 |
| Adipic Acid | 28.5 |
| Sodium Carbonate | 43 |
| Exemplary protease | 9 |
| Fatty alcohol polyglycol ether | 6.5 |
| Amine oxide | 4 |

To prepare the use solutions, 1000 mL of water was heated to 40° C. in a 1000 mL beaker, and detergent was added to make an RTU solution. The exemplary solid enzymatic manual instrument detergent was added in an amount to provide a concentration of about 660 ppm. The two commercially available comparative detergents (Prolystica 2X Enzymatic Presoak and Cleaner and Ruhof Endozime AW Triple Plus with APA) were added at a concentration of about 2000 ppm. The beakers were placed in a 40° C. water bath and continuously stirred with a 2 inch stir bar at about 300 RPM.

TOSI coupons from Healthmark, which are stainless steel coupons with simulated dried blood soil on them, were removed from their packaging and plastic casing, and one TOSI coupon was placed directly into each RTU solution to soak for 30 min. The TOSI coupons were placed facing the 1 inch wide vortex, approximately ½" from the center of the vortex, with the top (i.e., short side) of each coupon just under the surface of the water. Pictures of soil removal were taken at 5, 10, 15, 20, 25, and 30 min after each TOSI coupon was immersed in the solution. Each TOSI coupon was then removed from the solution, promptly rinsed in DI water, and allowed to air dry so that a final picture could be taken of the dried coupon.

Figure 4:
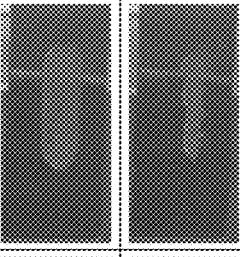
FIG. 4 are photographs comparing the removal of simulated surgical soils on TOSI for an exemplary solid enzymatic detergent composition against two comparative exemplary commercially available surgical instrument detergents.

The results are provided in FIG. 4. In FIG. 4, Competitive Formula A refers to Prolystica 2X Enzymatic Presoak and Cleaner, Competitive Formula B refers to Ruhof Endozime AW Triple Plus with APA, and Exemplary Formula A refers to the composition described in Table 19. As can be seen in FIG. 4, Competitive Formula A leaves persistent residue on the TOSI coupon and Competitive Formula B took 20-25 min to remove the simulated surgical soil. Exemplary Formula A provided the best performance only taking about 10-15 min to remove the simulated surgical soil.

Example 9

To test the compatibility and effect of having a combination of enzymes in a composition, a use solution comprising a detergent (shown in Table 20) and both an exemplary commercially available protease and exemplary commercially available amylase were prepared and tested. Melamine tiles were soiled with baked-on cheese. The reflectance values of the soiled melamine tiles were measured with a Hunter colorimeter. These exemplary use solutions were tested against a control use solution having just the detergent and a use solution comprising the detergent and only the exemplary protease. The use solutions were prepared according to Table 21 below.

TABLE 20

|  | Composition A (wt. %) |
| --- | --- |
| Phosphonate | 1-5 |
| KOH | 1-5 |
| Acusol 448 | 3-7 |
| Acusol 445ND | 1-5 |
| Nonionic Surfactant | 1-5 |
| Sodium Carbonate | 50-60 |
| Acid | 25-30 |

TABLE 21

|  | Use Solution (ppm) | | | |
| --- | --- | --- | --- | --- |
|  | Control | A | B | C |
| Detergent | 400 | 400 | 400 | 400 |
| Protease | 0 | 8 | 8 | 8 |
| Amylase | 0 | 0 | 10 | 5 |

Figure 5:
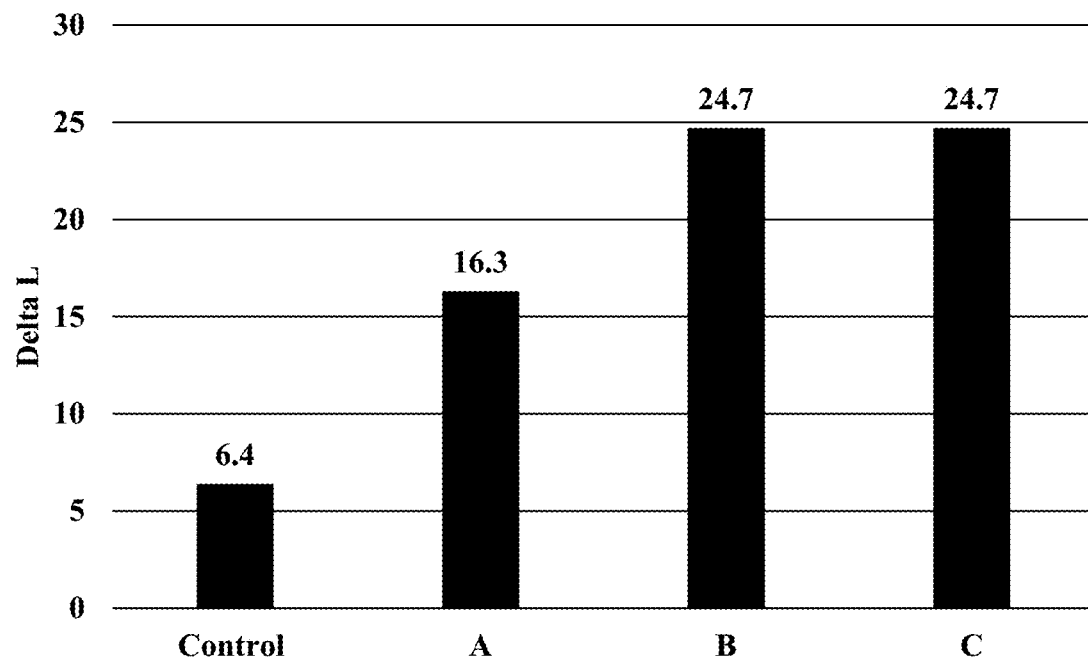
FIG. 5 is a bar chart comparing the soil removal performance of a use solution comprising a detergent composition without an enzyme, comprising a protease, and comprising a protease and an amylase on melamine tiles soiled with baked cheese.

The soiled tiles were soaked in the use solution for about 40 minutes at a temperature of about 160° F. The tiles were rinsed with water and the reflectance values were measured for the cleaned tiles. The difference between the soiled reflectance values and the clean reflectance values was then calculated and is shown FIG. 5. As can be seen in FIG. 5, all of the use solutions comprising an enzyme provided superior cleaning performance when contrasted with the control. Moreover, the use solutions comprising both a protease and an amylase provided superior cleaning performance compared with the use solution having only a protease.

Example 10

Exemplary use solutions were prepared comprising an exemplary protease and other components of the solid cleaning compositions to the impact of the different components on the enzymes performance to ensure compatibility. The use solutions were prepared according to Table 22 below.

TABLE 22

|  | Use Solution (ppm) | | | | | |
| --- | --- | --- | --- | --- | --- | --- |
|  | Control | A | B | C | D | E |
| EDTA | 180 | 180 | 180 | 180 | 180 | 180 |
| Sodium Carbonate | 256 | 256 | 256 | 256 | 256 | 256 |
| PH | 9.8 | 9.8 | 9.8 | 9.8 | 9.8 | 9.8 |
| Protease | 10 | 10 | 10 | 10 | 10 | 10 |
| Acusol 448 | 0 | 12.5 | 0 | 0 | 0 | 12.5 |
| Acusol 445 | 0 | 0 | 12.5 | 0 | 0 | 12.5 |
| Phosphonate | 0 | 0 | 0 | 7.5 | 0 | 7.5 |
| Nonionic Surfactant | 0 | 0 | 0 | 0 | 10 | 10 |

Figure 6:
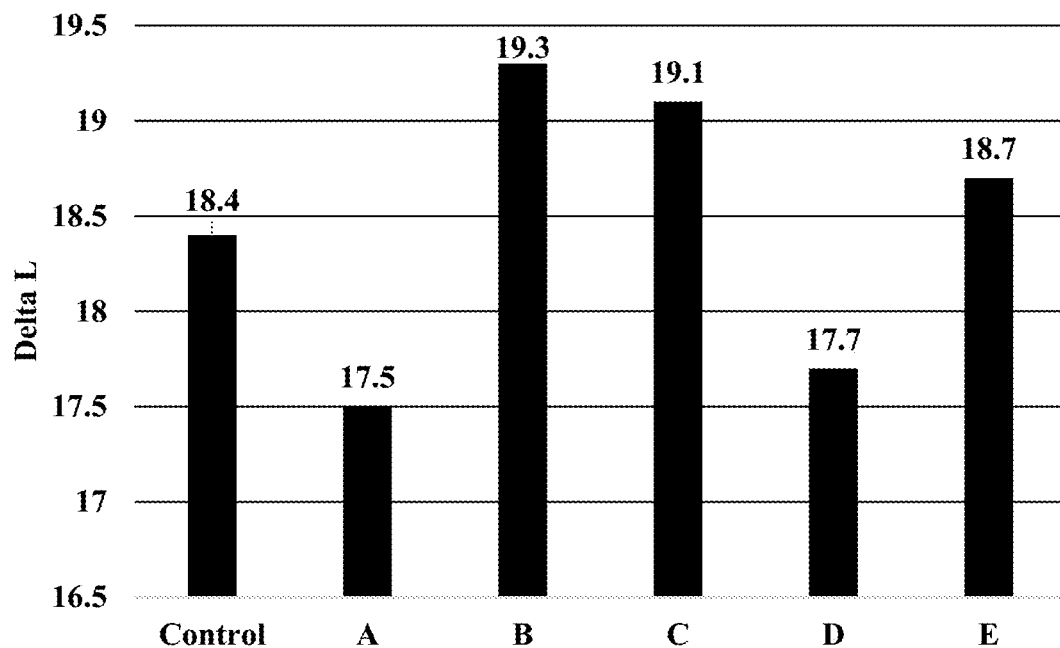
FIG. 6 is a bar chart assessing the compatibility of various components with an exemplary protease based on the effect on soil removal performance on melamine tiles soiled with baked cheese.

The soiled tiles were soaked in the use solution for about 1 hour at a temperature of about 160° F. The tiles were rinsed with water and the reflectance values were measured for the cleaned tiles. The difference between the soiled reflectance values and the clean reflectance values was then calculated and is shown FIG. 6. As can be seen in FIG. 6, the components tested did not significantly impact the performance of the enzyme indicating their compatibility. Even in the instances where the enzyme performance was lower, it was only minimal and the use solution comprising all of the tested components (Use Solution E) provided better performance than the control.

The inventions being thus described, it will be obvious that the same may be varied in many ways. Such variations are not to be regarded as a departure from the spirit and scope of the inventions and all such modifications are intended to be included within the scope of the following claims. Since many embodiments can be made without departing from the spirit and scope of the invention, the invention resides in the claims.

What is claimed is:

1. A solid detergent composition comprising:
a solidification matrix comprising an alkali metal carbonate and between about 12 wt. % and about 50 wt. % of an acid based on the weight of the composition, wherein the acid has an aqueous solubility of between 0.1 and 1500 g/L at 20° C., and wherein the acid is a polycarboxylic acid comprising adipic acid, glutamic acid, citric acid, isocitric acid, glutaric acid, malic acid, propane-1,2,3-tricarboxylic acid, succinic acid, tartaric acid, salts of the foregoing, or a mixture thereof;
an enzyme; and
a surfactant, wherein the surfactant is a nonionic surfactant, amphoteric surfactant, or a mixture thereof;
wherein the composition is substantially free of added water and fatty acids; and
wherein upon dilution the composition provides a pH of between about 6 and about 10; wherein the solid is a cast solid, extruded solid, molded solid, a powder, or pressed solid.

2. The composition of claim 1, wherein the alkali metal carbonate is in an amount between about 15 wt. % and about 75 wt. % of the composition.

3. The composition of claim 1, wherein the acid is in an amount between about 15 wt. % and about 50 wt. % of the composition.

4. The composition of claim 1, wherein the enzyme is in an amount between about 0.1 wt. % and about 25 wt. %; and wherein the enzyme is a protease, lipase, amylase, cellulase, or a mixture thereof.

5. The composition of claim 1, wherein the surfactant is in an amount between about 0.5 wt. % and about 25 wt. %; and wherein the surfactant is a surfactant having (PO)(EO)(PO) structure and a molecular weight of less than 3000 g/mole, an EO/PO capped alkoxylated glycerol, a polyol, a dimethyl amine, a betaine, a branched alcohol alkoxylate, an alkyl polyglucoside, or mixtures thereof.

6. The composition of claim 1, further comprising one or more of the following an alkalinity source, an aminocarboxylate, a corrosion inhibitor, a defoamer, a dye, an enzyme stabilizer, a fragrance, a phosphonate, a preservative, a water conditioning agent, and combinations thereof.

7. The composition of claim 1, wherein the solid is a pressed solid.

8. The composition of claim 1, wherein the composition is low foaming and removes soils comprising blood at temperatures between about 50° F. and about 150° F.

9. A method of cleaning a surface comprising:
diluting the solid detergent composition of claim 1 to form a cleaning solution, wherein the cleaning solution has a concentration of between about 300 ppm to about 1800 ppm;
contacting a surface with the cleaning solution;
rinsing the surface with water.

10. The method of claim 9, further comprising a presoak step prior to the contacting step.

11. The method of claim 9, wherein the diluting step is at a dilution ratio of between about 1/32 oz/gal and about 1 oz/gal.

12. The method of claim 9, wherein the surface is an instrument, wherein the instrument is soiled with blood and/or human tissue; wherein the blood and/or human tissue are removed from the instrument during the contacting and/or rinsing steps; wherein the contacting step is performed at a temperature between about 50° F. and about 150° F.; and wherein the cleaning solution has a concentration of between about 600 ppm and about 1250 ppm.

13. The method of claim 12, further comprising a disinfecting step; and wherein the disinfecting step is performed with a sanitizer and/or at a temperature greater than about 200° F.

14. The method of claim 12, wherein the surface is a ware; and wherein the cleaning solution has a concentration of between about 400 ppm and about 1350 ppm.

15. The method of claim 12, wherein the contacting step is performed at a temperature between about 60° F. and about 180° F.

16. A solid detergent composition comprising:
a solidification matrix comprising an alkali metal carbonate and a polycarboxylic acid or salt thereof, wherein the polycarboxylic acid has aqueous solubility between 0.1 and 1500 g/L at 20° C., wherein the alkali metal carbonate is between about 15 wt. % and about 75 wt. % of the composition, and wherein the polycarboxylic acid is between about 15 wt. % and about 50 wt. % of the composition, and wherein the polycarboxylic acid has between 2 and 4 carboxyl groups;
between about 0.1 wt. % and about 25 wt. % of an enzyme; and
between about 0.5 wt. % and about 25 wt. % of a surfactant, wherein the surfactant is a nonionic surfactant, amphoteric surfactant, or a mixture thereof;
wherein the composition is substantially free of added water and fatty acids; and
wherein upon dilution the composition provides a pH of between about 6 and about 10; and
wherein the composition is a cast solid, extruded solid, molded solid, a powder, or pressed solid.

17. The composition of claim 16, wherein the alkali metal carbonate is in an amount between about 20 wt. % and about 75 wt. % of the composition; and wherein the polycarboxylic acid or salt thereof is in an amount between about 20 wt. % and about 45 wt. % of the composition and comprises adipic acid, glutamic acid, citric acid, isocitric acid, glutaric acid, malic acid, propane-1,2,3-tricarboxylic acid, succinic acid, tartaric acid, salts of the foregoing, or a mixture thereof.

18. The composition of claim 16, wherein the enzyme is in an amount between about 0.5 wt. % and about 20 wt. %; and wherein the enzyme is a protease, lipase, amylase, cellulase, or mixture thereof.

19. The composition of claim 16, wherein the surfactant is in an amount between about 1 wt. % and about 10 wt. %; and wherein the surfactant is a surfactant having (PO)(EO)(PO) structure and a molecular weight of less than 3000 g/mole and a cloud point in a 1% aqueous solution greater than 30° C., an EO/PO capped alkoxylated glycerol, trimethylolpropane, an amine oxide, a dimethyl amine, a betaine, a branched alcohol alkoxylate, an alkyl polyglucoside, or a mixture thereof.

20. The composition of claim 16, further comprising an alkalinity source, an aminocarboxylate, a corrosion inhibitor, a defoamer, a dye, an enzyme stabilizer, a fragrance, a phosphonate, a preservative, a water conditioning agent, and mixtures thereof.

21. The composition of claim 16, further comprising a preservative in an amount between about 0.01 wt. % and about 2 wt. %; and a water conditioning agent in an amount between about 0.5 wt. % and about 20 wt. %.

22. The composition of claim 21, wherein the composition is low foaming or non-foaming, removes soils comprising blood at temperatures between about 50° F. and about 150° F., and upon dilution provides a pH of between about 6.5 and about 9.

23. The composition of claim 16, wherein the composition is a pressed solid.

* * * * *